(12) United States Patent
Veryasov et al.

(10) Patent No.: US 11,964,934 B2
(45) Date of Patent: Apr. 23, 2024

(54) PROCESS TO CONDUCT AN ENDOTHERMIC CATALYTIC CRACKING REACTION IN A FLUIDIZED BED REACTOR

(71) Applicant: TOTALENERGIES ONETECH, Courbevoie (FR)

(72) Inventors: Gleb Veryasov, Nivelles (BE); Nikolai Nesterenko, Nivelles (BE); Walter Vermeiren, Houthalen (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/016,843

(22) PCT Filed: Jul. 27, 2021

(86) PCT No.: PCT/EP2021/071034
§ 371 (c)(1),
(2) Date: Jan. 18, 2023

(87) PCT Pub. No.: WO2022/023359
PCT Pub. Date: Feb. 3, 2022

(65) Prior Publication Data
US 2023/0271900 A1    Aug. 31, 2023

(30) Foreign Application Priority Data

Jul. 28, 2020 (EP) .................................. 20315367

(51) Int. Cl.
*C07C 4/06* (2006.01)
*B01J 8/18* (2006.01)
(Continued)

(52) U.S. Cl.
CPC ............... *C07C 4/06* (2013.01); *B01J 8/1827* (2013.01); *B01J 8/1836* (2013.01); *B01J 8/28* (2013.01);
(Continued)

(58) Field of Classification Search
CPC ........ B01J 8/18; B01J 8/28; B01J 8/42; C07C 4/06; C10G 47/30
See application file for complete search history.

(56) References Cited

U.S. PATENT DOCUMENTS 2,982,622 A    5/1961   Jahnig et al.
3,254,957 A    6/1966   Meiers et al.

FOREIGN PATENT DOCUMENTS

WO         2019/145279 A1      8/2019
WO    WO-2019145279 A1 *       8/2019    ................ B01J 8/24

OTHER PUBLICATIONS

International Search Report dated Oct. 27, 2021 issued in corresponding International Application No. PCT/EP2021/071034.
(Continued)

*Primary Examiner* — Sharon Pregler
(74) *Attorney, Agent, or Firm* — Nath, Goldberg & Meyer; Joshua B. Goldberg

(57) ABSTRACT

The disclosure relates to a process to perform a catalytic cracking reaction of hydrocarbons having at least four carbons, said process comprising the steps of providing a fluidized bed reactor comprising at least two electrodes and a bed comprising particles, wherein the particles are put in a fluidized state to obtain a fluidized bed; heating said bed to a temperature between 500° C. and 850° C. by passing an electric current through the fluidized bed to conduct the reaction. The process is remarkable in that the particles of the bed comprise electrically conductive particles and particles of a catalytic composition, wherein at least 10 wt. %
(Continued)

of the particles are electrically conductive particles and have a resistivity from 0.001 to 500 Ohm.cm at 500° C. and in that the step of heating the fluidized bed is performed by passing an electric current through the fluidized bed.

20 Claims, 3 Drawing Sheets

(51) Int. Cl.
*B01J 8/28* (2006.01)
*B01J 8/42* (2006.01)
*C10G 47/30* (2006.01)

(52) U.S. Cl.
CPC ................ *B01J 8/42* (2013.01); *C10G 47/30* (2013.01); *B01J 2208/00398* (2013.01); *B01J 2208/00805* (2013.01); *C07C 2529/06* (2013.01); *C10G 2400/20* (2013.01); *C10G 2400/30* (2013.01)

(56) References Cited

OTHER PUBLICATIONS

International Preliminary Report of Patentability dated Jul. 26, 2022 issued in corresponding International Application No. PCT/EP2021/071034.

\* cited by examiner

PROCESS TO CONDUCT AN ENDOTHERMIC CATALYTIC CRACKING REACTION IN A FLUIDIZED BED REACTOR

This is a National Phase Application filed under 35 U.S.C. 371 as a national stage of PCT/EP2021/071034, filed Jul. 27, 2021, an application claiming the benefit of European Application No. 20315367.1, filed Jul. 28, 2020, the content of each of which is hereby incorporated by reference in its entirety.

TECHNICAL FIELD

The present disclosure relates to a process for performing an endothermic catalytic cracking reaction in an installation comprising at least one fluidized bed reactor, the process is performed without the need of an external heating device in the said fluidized bed reactor. The present disclosure aims to contribute to the replacement of the use of fossil carbon-based fuels heating devices. The present disclosure relates to the electrification of the chemical industry.

TECHNICAL BACKGROUND

Climate change and ongoing energy transition make it mandatory to replace fossil carbon-based fuels in chemical production and recycled processes with a more environmentally friendly decarbonized source of energy. Transforming natural gas into valuable chemicals requires elevated temperature, often higher than 500° C. and even up to 1000° C. and are often endothermic. The energy needed is, therefore, high and not often environmentally friendly, as is demonstrated by the common use of fired heated reactors. Several studies have been undertaken to reduce the burden imposed by these (harsh) reaction conditions.

The study of Asensio J. M. et al., entitled "Hydrodeoxygenation using magnetic induction: high-temperature heterogeneous catalysis in solution" (Angew. Chem. Int. Ed., 2019, 58, 1-6) describes the use of magnetic nanoparticles as heating agents to improve the energy efficiency of reactions performed at high temperature, as the heat can be then directly and homogeneously transferred to the medium without the need for heating the reactor walls. This was applied in the hydrodeoxygenation of ketones. However, in such a system, relatively low temperatures up to 280° C. were reached and the reaction is exothermic.

In the study of Wismann S. T. et al., entitled "Electrified methane reforming: A compact approach to greener industrial hydrogen production" (Science, 2019, 364, 756-759), a conventional fired reactor was replaced by an electric-resistance-heated reactor. A laboratory-scale reactor based on FeCrAl alloy tube having a diameter of 6 mm and coated with a 130 μm nickel-impregnated washcoat was used to carry out steam methane reforming. As the heat source and the wall of the tube are one, it is possible to minimize the loss of heat and then to render more efficient and more economical the process of steam methane reforming. Temperatures with a maximum of 800° C. were reached with this kind of reactor.

In the study of Malerod-Fjeld H. et al., entitled "Thermo-electrochemical production of compressed hydrogen from methane with near-zero energy loss" (Nat. Energy, 2017, 2, 923-931), a ceramic tube, having an outer diameter of 1 cm and made of a perovskite derivative, is used as the electrolyte. By applying a voltage and hence a current across the electrolyte, hydrogen can be selectively extracted from methane and steam. The perovskite derivative is supplemented with nickel nanoparticles to provide the catalyst necessary for the reaction.

In the study of Varsano F. et al., entitled "Dry reforming of methane powered by magnetic induction" (Int. J. of Hydrogen Energy, 2019, 44, 21037-21044), electromagnetic induction heating of catalytic heterogeneous processes was used and has been demonstrated as bringing several advantages in terms of process intensification, energy efficiency, reactor setup simplification and safety issues coming from the use of radiofrequency. Temperatures ranging between 850° C. and 900° C. in reactors having 1 cm of inner diameter can be reached using $Ni_{60}Co_{60}$ pellets as heat mediators in a continuous-flow fixed-bed reactor.

These examples show that progress exists in the field of transforming fossils sources into valuable chemicals with the perspective to diminish the impact on the climate. However, this progress has not been developed to a large scale as it is rather limited to the laboratory environment.

With regards to this matter, the Shawinigan process, described in CA 573348, relates to a process to prepare hydrocyanic acid from ammonia using in a fluidized bed reactor made of high temperature-resistant silica glass and comprising conductive carbon particles, such as coke and/or petroleum coke. The principle resides in that the electricity is used to heat the conductive carbon particles which can maintain the fluidized bed at a temperature sufficient to transform ammonia into hydrocyanic acid, which is then recovered from the outgoing gas coming off the fluidized bed. The inner diameter of the reactor tube was 3.4 cm. A temperature ranging between 1300° C. and 1600° C., sufficient to perform the requested reaction, can be reached by using such conductive carbon particles.

U.S. Pat. No. 2,982,622 describes a method for producing hydrogen and high quality coke which comprises passing inert solid particles as a relatively dense mass downwardly through an elongated reaction zone, applying an electrical voltage of 0.1 to 1000 volts per inch across at least a portion of said solids mass in said reaction zone, said voltage being sufficient to raise the temperature of said solids to 1800° F. to 3000° F. due to their resistance to the flow of electricity without causing substantial electrical spark discharges through said solids mass, downwardly withdrawing thus heated solids from said reaction zone, preheating a hydrocarbon feed by heat exchange with said withdrawn solids and introducing said preheated feed into and upwardly through said reaction zone in the form of an upwardly moving gasiform stream, said feed contacting said heated solids and being converted to light vapors including a substantial portion of hydrogen and carbon which deposits on said solids, heat exchanging hot vapors withdrawn from said reaction zone with inert solids in a heating zone, circulating at least a portion of the solids withdrawn from the reaction zone and previously heat exchanged with said feed to said heating zone, passing solids from said heating zone to said reaction zone as solids feed thereto, and recovering at least a portion of the solids withdrawn from the reaction zone as product and recovering hydrogen gas and light vapors from the upper portion of said reaction zone.

U.S. Pat. No. 3,259,565 describes a process for converting hydrocarbons to produce lower boiling hydrocarbons and solid coke particles of a size larger than fluidizable size which comprises passing coke agglomerates down through a hot fluidized bed of coke particles, introducing hydrocarbon oil feed into said fluidized bed to crack the hydrocarbon oil, passing cracked vaporous products overhead, removing coke agglomerates from said fluid bed and passing them down through a heat exchanger zone in counter-current contact with said withdrawn cracked vaporous products to cool said cracked vaporous products and to heat said coke agglomerates while condensing and depositing higher boiling hydrocarbons from said cracked vaporous products on said coke agglomerates, withdrawing resulting cracked vaporous products as product, recirculating the so treated coke agglomerates a number of times through said heat exchange zone to deposit hydrocarbons and through said hot fluidized coke bed to coke the deposited high boiling hydrocarbons and to increase the size of the coke agglomerates, withdrawing coke agglomerates of increased size as product from the system.

The disclosure of US 2017/0158516 described a fluidized-bed reactor made of silicon carbide for preparing granular polycrystalline silicon at the industrial level. The fluidized-bed reactor is heated using a heating device which is placed in an intermediate jacket between the outer wall of the reactor tube and the inner wall of the reactor vessel. Such intermediate jacket comprises an insulation material and is filled or flushed with an inert gas. It was found that the use of sintered silicon carbide (SSiC) having a SiC content of 98% by weight as the main element of the reactor tube with a high purity SiC coating deposited by chemical vapour deposition allowed reaching high temperature up to 1200° C. without the tube being corroded.

It was also found that using siliconized silicon carbide (SiSiC) as the main element of the reactor tube without any surface treatment, such as the deposition of a coating layer, led to the tube being corroded.

On the other hand, the disclosure of Goldberger W. M. et al., entitled "*The electrothermal fluidized bed*" (*Chem. Eng. Progress,* 1965, 61 (2), 63-67, relates to fluidized-bed reactor made in graphite and susceptible to perform reactions such as the hydrocracking of hydrocarbons, the pyrolysis of organics, the production of elemental phosphorus or the chlorination of zirconium oxide. Operation at temperatures up to about 4400° C. appears possible. However, it is not certain that from the long-term perspective, the graphite material used to design the fluidized-bed reactor can resist such harsh reaction conditions. Indeed, in the study of Uda T. et al., entitled "*Experiments on high temperature graphite and steam reactions under loss of coolant accident conditions*", (*Fusion Engineering and Design,* 1995, 29, 238-246), it has been shown that graphite corrodes under conditions involving steam and elevated temperature, for instance between 1000° C. and 1600° C. Also, as shown in the study of Qiao M-X. et aL, entitled "*Corrosion of graphite electrode in electrochemical advanced oxidation processes: degradation protocol and environmental application*", (*Chem. Eng. J.,* 2018, 344, 410-418), the graphite is susceptible to carbon oxidation reaction, which impacts in its activity as an electrode by restricting notably the voltage that can be applied to it.

Production of light olefins such as ethylene and propylene constitute the basis of many petrochemical processes, has been achieved mainly through thermal cracking of hydrocarbons. However, it requires very high temperatures over 800 to 900° C., emits a lot of $CO_2$ and provides limited control over the propylene/ethylene (P/E) ratio while the demand for propylene increases faster. Many catalytic processes focusing on "on purpose" light olefin production have been developed to supplement the demand such as propane dehydrogenation, methanol to olefins, olefin metathesis and catalytic cracking of olefins or of naphtha.

Thermal cracking is a function of temperature and time. The reaction occurs when hydrocarbons in the absence of a catalyst are exposed to high temperatures in the range of 800-900° C. The initial step in the chemistry of thermal cracking is the formation of free radicals. They are formed upon splitting the C—C bond. The rupturing produces two uncharged species which share a pair of electrons. Free radicals are extremely reactive and short-lived. They can undergo alpha-scission, beta-scission, and polymerization.

Conventional steam crackers are complex industrial facilities that can be divided into three main zones, each of which has several types of equipment with very specific functions:

(i) the hot zone including cracking furnaces, quench exchanger and quench loop, the columns of the hot separation train;

(ii) the compression zone including a cracked gas compressor, purification and separation columns, dryers and (iii) the cold zone including the cold box, de-methaniser, fractionating columns of the cold separation train, the C2 and C3 converters, the gasoline hydrostabilization reactor.

Conventional steam cracking is carried out in tubular reactors in direct-fired heaters (furnaces). Various tube sizes and configurations can be used, such as a coiled tube, U-tube, or straight tube layouts. Tube diameters range from 2.5 cm to 25 cm. Each furnace comprises a convection zone in which the waste heat is recovered and a radiant zone in which cracking takes place.

The cracking of hydrocarbons is generally catalyzed by acid catalyst via a carbocation mechanism. Hence, stability of the intermediate carbocation will determine the end product distribution: order of stability is: tertiary>secondary>primary cations and the higher the temperature the higher less stable intermediates can be produced see study entitled "*Thermodynamic analysis of catalytic cracking reactions as the first stage in the development of mathematical description*", by Nazarova G., et al. (*Procedia Chemistry,* 2015, 15, 342-349).

Light olefins may be produced in the fluid cracking catalytic (FCC) unit of the crude oil refinery. Such an FCC process is a catalytic cracking technique using a catalyst in the form of fine particles which can are fluidized when being aerated using gaseous fluid. Especially, to increase the yield of olefin (e.g., propylene) instead of gasoline additives like ZSM-5 zeolites are used or particular operating conditions like long residence time and high reaction temperature applied in DCC (Deep Catalytic Cracking) is known as a modification of the FCC process to boost light olefin make. In the FCC process, a vacuum residue, an atmospheric residue, or gas oil are used as the feedstock that makes sufficient coke that provides the required reaction heat when burned in the regenerator. However, FCC suffers because olefins are produced as the by-product and the required reaction energy is supplied by the combustion of the coke deposited on the catalyst that allows reheating the circulating catalyst.

U.S. Pat. No. 3,758,403 discloses that the method by adding ZSM-5 Zeolite in the FCC catalyst might increase the octane number of gasoline and the yield of light olefins: when adding 1.5, 2.5, 5 and 10% ZSM-5 Zeolite to the conventional catalyst with 10% REY zeolite, the octane number of gasoline is increased and the yield of light olefin is increased. U.S. Pat. No. 5,997,728 discloses a method in which a shape-selective cracking addition agent is used in large amounts in the FCC process of heavy feedstock. The additives comprise from 12 to 40% amorphous matrix and at least 10% ZSM-5 Zeolite. This method increases light olefins yield, without increasing the yield of aromatics. The cracking activity and hydrothermal stability of ZSM-5 Zeolite are increased by modifying the ZSM-5 Zeolite by phosphorous compounds.

EP 1036133 B1 relates to a process for the catalytic cracking of an olefin-rich feedstock which is selective towards light olefins in the effluent, the process comprising contacting a hydrocarbon feedstock containing one or more olefins, with an MFI-type crystalline silicate catalyst having a silicon/aluminium atomic ratio of at least about 300 at an inlet temperature of from 500 to 600° C., at an olefin partial pressure of from 0.01 to 0.2 MPa and the feedstock being passed over the catalyst at an LHSV of from 10 to 30 h-1, to produce an effluent with an olefin content of lower molecular weight than that of the feedstock.

Zhao G. et al. have described a series of H-ZSM-5 catalysts with various phosphorus (P) loadings in "*Effect of phosphorus on HZSM-5 catalyst for $C_4$-olefin cracking reactions to produce propylene*" (*J. of Catalysis*, 2007, 248 (1), 29-37).

The present disclosure aims to provide a large-scale solution to one or more of the problems encountered in the prior art that is suitable for application in the industry, such as the chemical industry. The present disclosure aims to contribute to the replacement of the use of fossil carbon-based fuels heating devices in fluidized bed reactors. The present invention provides a solution to conduct endothermic hydrocarbons catalytic cracking into a mixture of light olefins and optionally aromatics.

SUMMARY

According to a first aspect, the disclosure provides for a process to perform an endothermic catalytic cracking reaction of one or more hydrocarbons having at least four carbons, said process comprising the steps of:
a) providing at least one fluidized bed reactor comprising at least two electrodes and a bed comprising particles;
b) putting the particles of the bed in a fluidized state by passing upwardly through the said bed a fluid stream, to obtain a fluidized bed;
c) heating the fluidized bed to a temperature ranging from 500° C. to 850° C. to conduct the endothermic catalytic cracking reaction of one or more hydrocarbons having at least four carbons;
d) optionally recovering the cracking products of the reaction;
the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm.cm to 500 Ohm.cm at 500° C. and in that the step (c) of heating the fluidized bed is performed by passing an electric current through the fluidized bed.

For example, the fluid stream provided in step b) comprises hydrocarbon feedstock, in which the hydrocarbons have at least four carbons, and optionally steam. The fluid stream may be a gaseous stream and/or a vaporized stream.

It is preferred that the at least one fluidized bed reactor comprising at least two electrodes and a bed comprising particles is devoid of packing.

Surprisingly, it has been found that the use of electrically conductive particles such as silicon carbide, mixed oxides, and/or mixed sulphides, said mixed oxides and/or said mixed sulphides being ionic or mixed conductor, namely being doped with one or more lower-valent cations, in one or more fluidized bed reactors which are electrified allows maintaining a temperature sufficient to carry out an endothermic catalytic cracking reaction requesting high-temperature reaction conditions such as temperature reaction ranging from 500° C. to 850° C. without the need of any external heating device. The use of at least 10 wt. % of electrically conductive particles within the particles of the bed allows minimizing the loss of heat when a voltage is applied. Thanks to the Joule effect, most, if not all, the electrical energy is transformed into heat that is used for the heating of the reactor medium.

In a preferred embodiment, the volumetric heat generation rate is greater than 0.1 MW/m$^3$ of fluidized bed, more preferably greater than 1 MW/m$^3$, in particular, greater than 3 MW/m$^3$.

In a preferred embodiment, at least one fluidized bed reactor is devoid of heating means; for example, at least one fluidized bed reactor comprises a vessel and is devoid of heating means located around or inside the vessel. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

The solid particulate material (i.e. the particles) used in the at least one fluidized bed reactor consists of solid particulates having electrical conductivity allowing generating heat and catalytic particulate material to catalyse the cracking of hydrocarbons. The catalytic particulate material can also be electrically conductive and hence contribute to the generation of heat for the endothermal cracking reaction.

The Electrically Conductive Particles of the Bed

For example, the content of electrically conductive particles is ranging from 10 wt. % to 100 wt. % based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %. In the case where the content of electrically conductive particles based on the total weight of the particles of the bed is 100 wt. %, at least a part of said electrically conductive particles are also catalytic particles.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %; and most preferably at least 30 wt. % or at least 40 wt. % or at least 50 wt. % or at least 60 wt. %.

For example, the electrically conductive particles have a resistivity ranging from 0.005 to 400 Ohm.cm at 500° C., preferably ranging from 0.01 to 300 Ohm.cm at 500° C.; more preferably ranging from 0.05 to 150 Ohm.cm at 500° C. and most preferably ranging from 0.1 to 100 Ohm.cm at 500° C.

For example, the electrically conductive particles have a resistivity of at least 0.005 Ohm.cm at 500° C.; preferably of at least 0.01 Ohm.cm at 500° C., more preferably of at least 0.05 Ohm.cm at 500° C.; even more preferably of at least 0.1 Ohm.cm at 500° C., and most preferably of at least 0.5 Ohm.cm at 500° C.

For example, the electrically conductive particles have a resistivity of at most 400 Ohm.cm at 500° C.; preferably of at most 300 Ohm.cm at 500° C., more preferably of at most 200 Ohm.cm at 500° C.; even more preferably of at most 150 Ohm.cm at 500° C., and most preferably of at most 100 Ohm.cm at 500° C.

The selection of the content of electrically conductive particles based on the total weight of the bed and of the electrically conductive particles of a given resistivity influence the temperature reached by the fluidized bed. Thus, in case the targeted temperature is not attained, the person skilled in the art may increase the density of the particle bed, the content of electrically conductive particles based on the total weight of the particles of the bed and/or select electrically conductive particles with a lower resistivity to increase the temperature reach by the fluidized bed.

For example, the density of the solid particles in the bed is expressed as the void fraction. Void fraction or bed porosity is the volume of voids between the particles divided by the total volume of the bed. At the incipient fluidisation velocity, the void fraction is typically between 0.4 and 0.5. The void fraction can increase up to 0.98 in fast fluidised beds with lower values at the bottom of about 0.5 and higher than 0.9 at the top of the bed. The void fraction can be controlled by the linear velocity of the fluidising gas and can be decreased by recycling solid particles that are recovered at the top and send back to the bottom of the fluidized bed, which compensates the entrainment of solid particles out of the bed.

The void fraction VF is defined as the volume fraction of voids in a bed of particles and is determined according to the following equation:

$$VF = \frac{Vt - Vp}{Vt} \quad (1)$$

wherein Vt is the total volume of the bed and is determined by $$Vt = AH \quad (2)$$

wherein A is the cross-sectional area of the fluidized bed and H is the height of the fluidized bed; and wherein Vp is the total volume of particles within the fluidized bed.

For example, the void fraction of the bed is ranging from 0.5 to 0.8; preferably ranging from 0.5 to 0.7, more preferably from 0.5 to 0.6. To increase the density of the particle bed, the void fraction is to be reduced.

For example, the particles of the bed have an average particle size ranging from 5 to 300 µm as determined by sieving according to ASTM D4513-11, preferably ranging from 10 to 200 µm and more preferably ranging from 20 to 200 µm or from 30 to 150 µm. For example, the electrically conductive particles of the bed have an average particle size ranging from 5 to 300 µm as determined by sieving according to ASTM D4513-11, preferably ranging from 10 to 200 µm and more preferably ranging from 20 to 200 µm or from 30 to 150 µm.

In an embodiment, from 50 wt. % to 100 wt. % of the electrically conductive particles of the bed based on the total weight of the electrically conductive particles of the bed are one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and/or any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more carbon-containing particles and one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

As an alternative, the electrically conductive particles of the bed are or comprise one or more particles selected from one or more metallic alloys, one or more non-metallic resistors, provided that the non-metallic resistor is not silicon carbide, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations and/or one or more and/or mixed sulphides being doped with one or more lower-valent cations and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more particles selected from one or more metallic alloys, one or more non-metallic resistors, one or more carbon-containing particles, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more carbon-containing particles and one or more selected from one or more metallic alloys, one or more non-metallic resistors, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more non-metallic resistors, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, one or more metallic alloys are selected from Ni—Cr, Fe—Ni—Cr, Fe—Ni—Al or a mixture thereof. With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

For example, a non-metallic resistor is silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof, preferably silicon carbide. In an alternative, said non-metallic resistors particles are selected from molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

For example, said one or more metallic carbides are selected from iron carbide ($Fe_3C$), molybdenum carbide (such as a mixture of MoC and $Mo_2C$).

For example, said one or more transition metal nitrides are selected from zirconium nitride (ZrN), tungsten nitride (mixture of $W_2N$, WN, and $WN_2$), vanadium nitride (VN), tantalum nitride (TaN), and/or niobium nitride (NbN).

For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, said one or more carbon-containing particles are selected from graphite, petroleum coke, carbon black, coke or a mixture thereof, preferably graphite.

For example, said one or more superionic conductors are selected from $LiAlSiO_4$, $Li_{10}GeP_2S_{12}$, $Li_{3-6}Si_{0.6}P_{0.4}O_4$, sodium superionic conductors (NaSICON), such as $Na_3Zr_2PSi_2O_{12}$, or sodium beta alumina, such as $NaAl_{11}O_{17}$, $Na_{1.6}Al_{11}O_{17.3}$, and/or $Na_{1.76}Li_{0.38}Al_{10.62}O_{17}$.

For example, said one or more phosphate electrolytes are selected from $LiPO_4$ or $LaPO_4$.

For example, said one or more mixed oxides are ionic or mixed conductors being doped with one or more lower-valent cations. Advantageously, said mixed oxides are doped with one or more lower-valent cations, and are selected from oxides having a cubic fluorite structure, perovskite or pyrochlore.

For example, said one or more mixed sulphides are ionic or mixed conductors being doped with one or more lower-valent cations.

For example, the electrically conductive particles of the bed are or comprise a non-metallic resistor being silicon carbide.

For example, the electrically conductive particles of the bed are or comprise silicon carbide. For example, the silicon carbide is selected from sintered silicon carbide, nitride-bounded silicon carbide, recrystallised silicon carbide, reaction bonded silicon carbide and any mixture thereof. The type of silicon carbide material is selected according to the required heating power necessary for supplying the reaction heat of the catalytic cracking.

For example, the electrically conductive particles of the bed are or comprise a mixture of a non-metallic resistor being silicon carbide and electrically conductive particles different from said silicon carbide. The presence of electrically conductive particles different from said silicon carbide in the bed is optional. It can be present as a starting material for heating the bed since it was found that the resistivity of silicon carbide at room temperature is too high to start heating the bed. Alternatively to the presence of electrically conductive particles different from silicon carbide, it is possible to provide heat to the reactor for a defined time to start the reaction.

For example, the silicon carbide is selected from sintered silicon carbide, nitride-bounded silicon carbide, recrystalised silicon carbide, reaction bonded silicon carbide and any mixture thereof. The type of silicon carbide material is selected according to the required heating power necessary for supplying the reaction heat of the catalytic cracking.

For example, the electrically conductive particles of the bed are or comprise a mixture of a non-metallic resistor being silicon carbide and electrically conductive particles different from said silicon carbide and the electrically conductive particles of the bed comprises from 10 wt. % to 99 wt. % of silicon carbide based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed comprise a mixture of a non-metallic resistor being silicon carbide and electrically conductive particles different from said silicon carbide, said electrically conductive particles different from said silicon carbide are one or more carbon-containing particles and/or one or more mixed oxides being doped with one or more lower-valent cations and/or one or more mixed sulphides being doped with one or more lower-valent cations; with preference, the carbon-containing particles are selected from graphite, carbon black, coke, petroleum coke and/or any mixture thereof.

For example, the electrically conductive particles of the bed are or comprise one or more mixed oxides being ionic conductor, namely being doped with one or more lower-valent cations; with preference, the mixed oxides being doped with one or more lower-valent cations are selected from:
  one or more oxides having a cubic fluorite structure being at least partially substituted with one or more lower-valent cations, preferentially selected from Sm, Gd, Y, Sc, Yb, Mg, Ca, La, Dy, Er, Eu; and/or
  one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or
  one or more $ABO_3$-perovskites with A bivalent cation and B tetra-valent cation, being at least partially substituted with one or more lower-valent cations, preferentially selected from magnesium (Mg), scandium (Sc), yttrium (Y), neodymium (Nd) or ytterbium (Yb) in the B position or with a mixture of different B elements in the B position; and/or
  one or more $A_2B_2O_7$-pyrochlore with A trivalent cation and B tetra-valent cation being substituted in A position with one or more lower-valent cation, preferentially selected from Ca or Mg and comprising at least one of Sn, Zr and Ti in B position.

Examples of One or More Mixed Sulphides are one or more sulphides having a cubic fluorite structure being at least partially substituted with one or more lower-valent cations, preferentially selected from Sm, Gd, Y, Sc, Yb, Mg, Ca, La, Dy, Er, Eu; and/or
  one or more $ABS_3$ structures with A and B tri-valent cations being at least partially substituted in A position with one or more lower-valent cations, preferably selected from Ca, Sr, or Mg, Sc, and comprising at least one of Ni, Ga, Co, Cr, Mn, Sc, Fe and/or a mixture thereof in B position; and/or
  one or more $ABS_3$ structures with A bi-valent cation and B tetra-valent cation, being at least partially substituted with one or more lower-valent cations, preferably selected from Mg, Sc, Y, Nd or Yb in the B position or with a mixture of different B elements in the B position; and/or
  one or more $A_2B_2S_7$ structures with A tri-valent cation and B tetra-valent cation, being at least partially substituted in A position with one or more lower-valent cations, preferably selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

For example, the electrically conductive particles of the bed are or comprise one or more metallic alloys; with preference, one or more metallic alloys are selected from Ni—Cr, Fe—Ni—Cr, Fe—Ni—Al or a mixture thereof.

With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

In the case where said electrically conductive particles different from said silicon carbide particles are particles are selected from non-metallic resistors, said non-metallic resistor is preferably molybdenum disilicide ($MoSi_2$).

For example, the electrically conductive particles of the bed are or comprise carbon-containing particles, said carbon-containing particle is preferably one or more selected from graphite, petroleum coke, coke and/or carbon black. For example, the electrically conductive particles of the bed are or comprise a mixture of silicon carbide particles and electrically conductive particles different from said silicon carbide particles wherein the electrically conductive particles different from said silicon carbide particles is or comprises graphite particles and one or more wherein the graphite particles have an average particle size ranging from 5 to 300 µm as determined by sieving according to ASTM D4513-11, more preferably ranging from 10 to 200 μm and most preferably ranging from 20 to 200 μm or from 30 to 150 μm.

The Particles of a Catalytic Composition

For example, the content of the particles of a catalytic composition based on the total weight of the particles of the bed is ranging from 30 wt. % to 100 wt. %; preferably from 32 wt. % to 95 wt. %, more preferably from 35 wt. % to 90 wt. %, even more preferably from 37 wt. % to 85 wt. %, most preferably from 40 wt. % to 80 wt. %, even most preferably from 45 wt. % to 75 wt. % or from 50 wt. % to 70 wt. %. In the case where the content of the particles of a catalytic composition based on the total weight of the particles of the bed is 100 wt. %, at least a part of said particles of a catalytic composition are also electrically conductive particles For example, the particles of a catalytic composition have an average particle size ranging from 5 to 300 μm as determined by sieving according to ASTM D4513-11, preferably ranging from 10 to 200 μm and more preferably ranging from 30 to 150 μm.

For example, the catalyst composition comprises (values are on dry final catalyst composition basis, balance to 100 wt. % being a binder) from 5.0 to 90.0 wt. % of one or more zeolites comprising at least one 10-membered ring channel and based on the total weight of the catalyst composition, preferably from 10.0 to 85.0 wt. %, more preferably from 20.0 to 80.0 wt. % and/or from 5.0 to 90.0 wt. % of one or more zeolites comprising pores with a diameter of at least 0.5 nm as determined by argon adsorption and based on the total weight of the catalyst composition, preferably from 10.0 to 85.0 wt. %, more preferably from 20.0 to 80.0 wt. %.

For example, the catalyst composition comprises a binder. With preference, said binder is one selected of silica, clays, such as clays from the kaolin family or clays from montmorillonite family and/or metal oxides, such as alumina.

One or more of the following features can be advantageously used to further define the one or more zeolites comprising at least one 10-membered ring channel:
said one or more zeolites comprise between at least one 10-membered ring channel and at least one 12-membered ring channel and/or comprise pore with a diameter between 0.5 nm and 1.5 nm, preferably between 0.52 nm and 0.95 nm, more preferably between 0.7 nm and 0.9 nm;
said one or more zeolites have a Si/Al molar ratio comprised between 20 and 5000, preferably between 50 and 4000, more preferably between 120 and 2000;
said one or more zeolites comprise from 0.01 to 10 wt. % of phosphorus based on the total weight content of said one or more zeolites;
said one or more zeolites comprise one or more metal compounds (M-comprising compounds) selected from group-11 elements (i.e. of group IB elements according to CAS system, group-11 elements being in accordance with new IUPAC system), preferably Ag, Au and/or Cu; group-4 elements (i.e. of group IVB elements according to CAS system, group-4 elements being in accordance with the new IUPAC system), preferably Ti and/or Zr; group-2 elements (i.e. of group IIA elements according to CAS system, group-2 elements being in accordance with the new IUPAC system), preferably Mg, Ca, Sr and/or Ba; one or more elements selected from Ce, Sn, Co, Mo, Mn, Ni, Fe, Cr, Pt, Pd, In, Ga, Re, W and V and/or one or more rare earth elements, preferably said one or more rare earth elements are selected from Dy, La, Pm, Sm, Sc, Yb and/or Y; with preference said one or more zeolites comprise one or more metal compounds in an amount ranging:
from 0.01 to 4.0 wt. % of group-11 elements based on the total weight content of said one or more zeolites, more preferably from 0.1 to 3.5 wt. %; and/or
from 0.5 to 10.0 wt. % of group-4 elements based on the total weight content of said one or more zeolites, more preferably from 1.0 to 8.0 wt. %; and/or
from 0.1 to 5.0 wt. % of group-2 elements based on the total weight content of said one or more zeolites, more preferably from 1.0 to 4.0 wt. %; and/or
from 0.005 to 5.0 wt. % of one or more elements selected from Ce, Sn, Co, Mo, Mn, Ni, Fe, Cr, Pt, Pd, In, Ga, Re, W and V and based on the total weight content of said one or more zeolites, more preferably from 0.01 to 4.5 wt. %; and/or
from 0.1 to 15.0 wt. % of one or more rare earth elements based on the total weight content of said one or more zeolites, more preferably from 1.0 to 10.0 wt. %;
said one or more zeolites are steamed, calcined, ion-exchanged, treated with acid solution and/or dealuminated.

A preferred zeolite from the above mentioned zeolites is a "medium pore size Zeolite" which is a zeolite having a pore size of from 0.5 to 0.65 nm as determined by argon adsorption, meaning a zeolite which has a pore size between the pore size of the small pore size zeolite (such as an A-type zeolite) and the pore size of the large pore size zeolite (such as a mordenite, an X-type zeolite and a Y-type zeolite), i.e., a zeolite comprising at least one 10-membered ring channel in the crystal framework thereof.

For example, the one or more zeolites are selected from the list comprising MFI, MEL, MTW, MTT and/or FER families, preferably from MFI, MEL and/or FER families. The one or more zeolites can also be selected among ZSM-8, ZSM-21 and/or ZSM-38, preferably among ZSM-8 and/or ZSM-38.

When the zeolite is selected from the MFI family, the zeolite is or comprises ZSM-5.
When the zeolite is selected from the MEL family, the zeolite is or comprises ZSM-11.
When the zeolite is selected from the MTW family, the zeolite is or comprises ZSM-12.
When the zeolite is selected from the MTT family, the zeolite is or comprises ZSM-23.
When the zeolite is selected from the FER family, the zeolite is or comprises ZSM-35.

Advantageously, the catalyst composition further comprises a catalyst support. With preference, said catalyst support is selected from the group comprising alumina, alumina sol, titania, zirconia, quartz, silica, silica sol, silica-alumina, silica-magnesia, silica-zirconia, silica-thoria, silica-beryllia, silica-titania, calcium-alumina, calcium-silicate, ceria-zirconia-alumina, ceria-titania-alumina, ceria-magnesia-alumina, calcium-silica-alumina, silica-alumina-zirconia, hafnia, lanthania, magnesia, ceria, zirconia stabilized with magnesia, zirconia stabilized with lanthania, zirconia stabilized with yttria, zirconia stabilized with ceria, alumina stabilized with lanthania, metal-aluminates, and mixture thereof. Example of metal aluminates are calcium aluminate and magnesium aluminate. Example of alumina are γ-alumina, δ-alumina, θ-alumina, and α-alumina. More preferably, said catalyst support is selected from alumina, alumina stabilized with lanthania, ceria-zirconia-alumina, ceria-titania-alumina and ceria-magnesia-alumina. Preferred support materials are those common materials (mentioned above) that can be used for resistive heating at the same time and which can be subdivided into metallic alloys and non-metallic resistors like silicon carbide (SiC) and molybdenum disilicide (MoSi$_2$), several mixed oxides with variable temperature optima and carbons like graphite. This latter option results in intimate contact between the catalytic active metal and the resistor particulate material.

The Endothermic Catalytic Cracking of Hydrocarbons

For example, the catalytic cracking reaction is conducted at a temperature ranging from 550° C. to 800° C., preferably from 600° C. to 750° C., more preferably from 650° C. to 700° C.

For example, the catalytic cracking reaction is performed at a pressure ranging between 0.1 MPa and 10.0 MPa, preferably between 0.5 MPa and 5.0 MPa.

In an embodiment, said process comprises a step of pre-heating with a gaseous stream said fluidized bed reactor before conducting said endothermic catalytic cracking reaction in the fluidized bed reactor; with preference, said gaseous stream is a stream of inert gas and/or has a temperature comprised between 500° C. and 800° C. The said embodiment is of interest when the electrically conductive particles of the bed have too high resistivity at room temperature to start the electro-heating of the bed.

For example, said endothermic catalytic cracking of hydrocarbons is performed at a weight hourly space velocity (defined as the ratio of mass flow of reaction stream to the mass of solid particulate material in the fluidized bed) of said reaction stream comprised between 0.1 h-1 and 100 h$^{-1}$, preferably comprised between 1.0 h$^{-1}$ and 50 h$^{-1}$, more preferably comprised between 1.5 h$^{-1}$ and 10 h$^{-1}$, even more preferably comprised between 2.0 h$^{-1}$ and 6.0 h$^{-1}$. The weight hourly space velocity is defined as the ratio of mass flow of the reaction stream to the mass of solid particulate material in the fluidized bed.

The hydrocarbon feedstock for the present process is selected from C4 hydrocarbons (olefins and paraffins), straight run naphtha, catalytic cracking naphtha (comprising olefins and paraffins), steam cracker pyrolysis gasoline, coker naphtha, and olefin rich by-products from methanol, dimethyl ether, methyl halide, methyl sulphide or di-methyl sulphide conversion or from Fischer-Tropsch synthesis.

With preference, the cracking products obtained in the present process may include one or more of ethylene, propylene and benzene, and optionally hydrogen, toluene, xylenes.

In a preferred embodiment, the outlet temperature of the reactor may range from 500 to 750° C., preferably from 550 to 700° C., more preferably from 600 to 650° C.

In a preferred embodiment, the catalytic cracking reaction performed on the hydrocarbon feedstock is done in presence of dilution steam in a ratio of 0.1 to 1.0 kg steam per kg of hydrocarbon feedstock, preferably from 0.15 to 0.7 kg steam per kg of hydrocarbon feedstock, more preferably in a ratio from 0.25 to 0.6 kg steam per kg of hydrocarbon feedstock, to obtain cracking products as defined above.

In a preferred embodiment, the catalytic cracking reaction is performed in the presence of hydrogen in a ratio of 0.1 to 5 mole hydrogen per mole of hydrocarbon feedstock, preferably from 0.2 to 3 and most preferably from 0.2 to 1.0.

In a preferred embodiment, the reactor outlet pressure may range from 0.050 to 0.250 MPa, preferably from 0.070 to 0.200 MPa, more preferably may be about 0.15 MPa. Lower operating pressure results in more light olefins yield and reduced coke formation. The lowest pressure possible is accomplished by (i) maintaining the output pressure of the reactor as close as possible to atmospheric pressure at the suction of the cracked gas compressor (ii) reducing the partial pressure of the hydrocarbons by dilution with steam (which has a substantial influence on slowing down coke formation).

Effluent from the catalytic cracking contains unreacted feedstock, desired olefins (mainly ethylene and propylene), hydrogen, methane, a mixture of C4's (gasoline (aromatics in the C6 to C8 range).

For example, the step of heating the fluidized bed is performed by passing an electric current at voltage of at most 300 V through the fluidized bed, preferably at most 200 V, more preferably at most 150 V, even more preferably at most 120 V, most preferably at most 100 V, even most preferably at most 90 V.

For example, said process comprises a step of pre-heating with a gaseous stream said fluidized bed reactor before conducting said catalytic cracking reaction in the fluidized bed reactor; with preference, said gaseous stream is a stream of inert gas and/or has a temperature comprised between 500° C. and 750° C.

For example, wherein the at least one fluidized bed reactor provided in step a) comprises a heating zone and a reaction zone and wherein the fluid stream provided in step b) is provided to the heating zone and comprises diluent gases, the step c) of heating the fluidized bed to a temperature ranging from 500° C. to 850° C. to conduct the catalytic cracking reaction of one or more hydrocarbons having at least four carbons comprises the following sub steps:
    heating the fluidized bed to a temperature ranging from 500° C. to 850° C. by passing an electric current through the heating zone of the at least one fluidized bed,
    transporting the heated particles from the heating zone to the reaction zone,
    in the reaction zone, putting the heated particles in a fluidized state by passing upwardly through the said bed of the reaction zone a fluid stream comprising one or more hydrocarbons having at least four carbons, and optional diluent gases to obtain a fluidized bed and to conduct the catalytic cracking reaction on the hydrocarbon feedstock,
    optionally, recovering the particles from the reaction zone and recycling them to the heating zone.

Step c) provides that the catalytic cracking reaction is performed on a hydrocarbon feedstock which implies that a hydrocarbon feedstock is provided.

For example, wherein the heating zone and the reaction zone are mixed (i.e. the same zone); the fluid stream provided in step b) comprises a hydrocarbon feedstock and optionally steam, the one or more hydrocarbons of the hydrocarbon feedstock having at least four carbons. The fluid stream may be a gaseous stream and/or a vaporized stream.

For example, wherein the heating zone and the reaction zone are separated zones, the fluid stream provided in step b) to the heating zone is devoid of a hydrocarbon feedstock. For example, wherein the process comprises providing at least one fluidized bed reactor being a heating zone and at least one fluidized bed reactor being a reaction zone, the fluid stream provided in step b) to the heating zone is devoid of a hydrocarbon feedstock and the fluid stream provided in step b) to the reaction zone comprises a hydrocarbon feedstock. The fluid stream may be a gaseous stream and/or a vaporized stream.

It is understood that the hydrocarbon feedstock is provided to the reaction zone and that when the heating zone is separated from the reaction zone, no hydrocarbon feedstock is provided to the heating zone. It is understood that in addition to the hydrocarbon feedstock provided to the reaction zone, steam can be provided to the reaction zone to reach the recommended steam to hydrocarbon ratio in the reaction zone as described above.

The Installation

According to a second aspect, the disclosure provides an installation to perform an endothermic catalytic cracking reaction on one or more hydrocarbons having at least four carbons, according to the first aspect, said installation comprising at least one fluidized bed reactor comprising:
- at least two electrodes, with preference, one electrode is a submerged central electrode or two electrodes are submerged electrodes;
- a reactor vessel;
- one or more fluid nozzles for the introduction of a fluidizing gas and/or of a reaction stream within at least one fluidized bed reactor; and
- a bed comprising particles;

the installation is remarkable in that the particles of the bed comprise electrically conductive particles and particles of a catalytic composition comprising one or more transition metals, wherein at least 10 wt. % of the particles based on the total weight of the particles of the bed are electrically conductive particles and have a resistivity ranging from 0.001 Ohm.cm to 500 Ohm.cm at 500° C.

Advantageously, at least one fluidized bed reactor is devoid of heating means. For example, at least one fluidized bed reactor comprises a reactor vessel and is devoid of heating means located around or inside the reactor vessel. For example, all the fluidized bed reactors are devoid of heating means. When stating that at least one of the fluidized bed reactors is devoid of "heating means", it refers to "classical" heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the fluidizing gas is one or more diluent gases.

For example, the at least one reactor vessel has an inner diameter of at least 100 cm, preferably at least 200 cm, more preferably at least 300 cm.

With preference, the reactor vessel comprises a reactor wall made of materials which are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ).

For example, the at least one fluidized bed reactor comprises a heating zone and a reaction zone, one or more fluid nozzles to provide a hydrocarbon feedstock to the reaction zone, and means to transport the particles from the heating zone to the reaction zone when necessary and optional means to transport the particles from the reaction zone back to the heating zone. This configuration is remarkable in that a given particle bed is common to more than one fluidized bed reactor. The common bed particle is distributed between at least two reactors and continuously moving from one reactor to another one.

For example, the installation comprises at least two fluidized bed reactors connected one to each other wherein at least one of said at least two fluidized bed reactors is the heating zone and at least another of said at least two fluidized bed reactors is the reaction zone. With preference, the installation comprises one or more fluid nozzles arranged to inject a hydrocarbon feedstock to the at least one fluidized bed reactor being the reaction zone.

For example, the at least one fluidized bed reactor is a single fluidized bed reactor wherein the heating zone is the bottom part of the fluidized bed reactor while the reaction zone is the top part of the fluidised bed reactor. With preference, the installation comprises one or more fluid nozzles to inject a hydrocarbon feedstock between the two zones.

For example, the at least one fluidized bed comprises at least two lateral zones being an outer zone and an inner zone wherein the outer zone is surrounding the inner zone, with the outer zone being the heating zone and the inner zone being the reaction zone. In a less preferred configuration, the outer zone is the reaction zone and the inner zone is the heating zone. With preference, the installation comprises one or more fluid nozzles to inject a hydrocarbon feedstock in the reaction zone.

With preference, one of the electrodes is the reactor vessel or the gas distributor and/or said at least two electrodes are made in stainless steel material or nickel-chromium alloys or nickel-chromium-iron alloys.

For example, the process is according to the first aspect.

The Use of a Particle Bed

According to a third aspect, the invention provides the use of a bed comprising particles in at least one fluidized bed reactor to perform a process of catalytic cracking of one or more hydrocarbons having at least four carbons according to the first aspect, the use is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm.cm to 500 Ohm.cm at 500° C.

For example, the use comprises heating the bed comprising particles to a temperature ranging from 500° C. to 850° C. in a first reactor, transporting the heated particle bed from the first reactor to a second reactor and providing a hydrocarbon feedstock to the second reactor; with preference, at least the second reactor is a fluidized bed reactor and/or at least the second reactor is devoid of heating means; more preferably, the first reactor and the second reactor are fluidized bed reactors and/or the first and the second reactor are devoid of heating means. For example, at least the second reactor is devoid of heating means selected from ovens, gas burners, hot plates, or any combination thereof. For example, the first and the second reactors are devoid of heating means selected from ovens, gas burners, hot plates, or any combination thereof.

According to a fourth aspect, the invention provides the use of an installation comprising at least one fluidized bed reactor to perform a catalytic cracking reaction, remarkable in that the installation is according to the second aspect. With preference, the use of an installation at least one fluidized bed reactor to perform a catalytic cracking reaction in a process according to the first aspect.

The particular features, structures, characteristics or embodiments may be combined in any suitable manner, as would be apparent to a person skilled in the art from this disclosure, in one or more embodiments.

DETAILED DESCRIPTION

Figure 1:
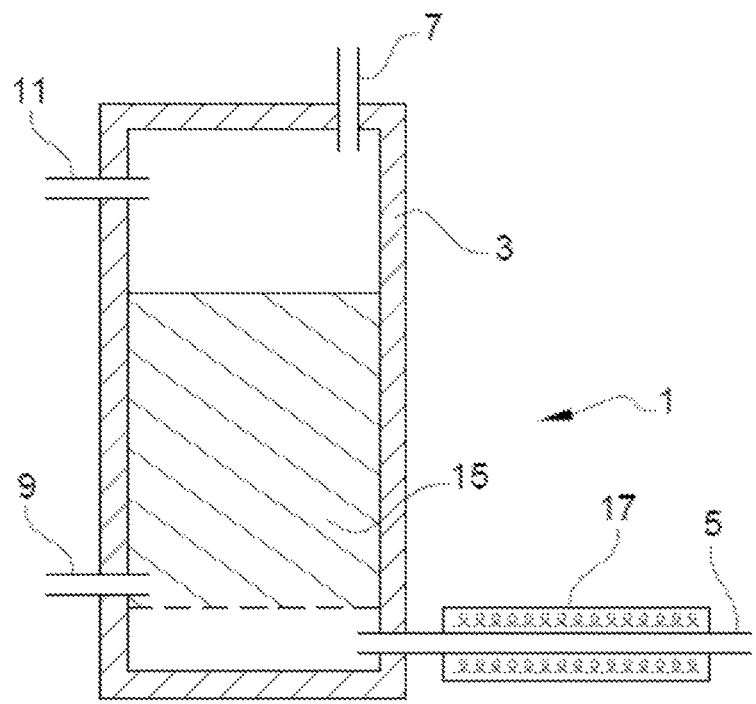
FIG. 1 illustrates an installation according to prior art.

For the disclosure, the following definitions are given:

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

Conventional catalytic cracking reactors can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The present disclosure recommends using a fluidized bed reactor using particles that are conductive enough to be able to generate heat by applying an electric current to the endothermic cracking the hydrocarbons. Online or periodic regeneration of the catalyst may be provided by any suitable means known in the art.

The present disclosure provides for a process to perform an endothermic catalytic cracking reaction of one or more hydrocarbons having at least four carbons, said process comprising the steps of:

a) providing at least one fluidized bed reactor comprising at least two electrodes and a bed comprising particles;

b) putting the particles of the bed in a fluidized state by passing upwardly through the said bed a fluid stream, to obtain a fluidized bed;

c) heating the fluidized bed to a temperature ranging from 500° C. to 850° C. to conduct the endothermic catalytic cracking reaction of one or more hydrocarbons having at least four carbons;

d) optionally recovering the cracking products of the reaction;

the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm.cm to 500 Ohm.cm at 500° C. and in that the step c) of heating the fluidized bed is performed by passing an electric current through the fluidized bed.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

The solid particulate material (i.e. the particles) in the fluidized bed reactor is typically supported by a porous plate, a perforated plate, a plate with nozzles or chimneys, known as a distributor. The fluid is then forced through the distributor up and travelling through the voids between the solid particulate material. At lower fluid velocities, the solids remain settled as the fluid passes through the voids in the material, known as a packed bed reactor. As the fluid velocity is increased, the particulate solids will reach a stage where the force of the fluid on the solids is enough to counterbalance the weight of the solid particulate material. This stage is known as incipient fluidization and occurs at this minimum fluidization velocity. Once this minimum velocity is surpassed, the contents of the reactor bed begin to expand and become fluidized. Depending on the operating conditions and properties of solid phase various flow regimes can be observed in such reactors. The minimum fluidization velocity needed to achieve bed expansion depends upon the size, shape, porosity and density of the particles and the density and viscosity of the upflowing fluid. (P. R. Gunjal, V. V. Ranade, in Industrial Catalytic Processes for Fine and Specialty Chemicals, 2016).

Four different categories of fluidization based on the mean particle have been differentiated by Geldart that determine the fluidization regimes:

type A, aeratable fluidization (medium size, medium-density particles which are easier to fluidize; Particles of typically 30-100 µm, density~1500 kg/m$^3$);

type B, sand-like fluidization (heavier particles which are difficult to fluidize; Particles of typically 100-800 µm, density between 1500 and 4000 kg/m$^3$);

type C, cohesive fluidization (typical powder-like solid particle fluidization; Fine-size particles (~20 µm) with a dominance of intraparticle or cohesive forces); and type D, spoutable fluidization (large density and larger particle~1-4 mm, dense and spoutable).

Fluidization may be broadly classified into two regimes (Fluid Bed Technology in Materials Processing, 1999 by CRC Press): homogeneous fluidization and heterogeneous fluidization. In homogeneous or particulate fluidization, particles are fluidized uniformly without any distinct voids. In heterogeneous or bubbling fluidization, gas bubbles devoid of solids are distinctly observable. These voids behave like bubbles in gas-liquid flows and exchange gas with the surrounding homogeneous medium with a change in size and shape while rising in the medium. In particulate fluidization, the bed expands smoothly with substantial particle movement and the bed surface is well defined. Particulate fluidization is observed only for Geldart-A type particles. A bubbling fluidization regime is observed at much higher velocities than homogeneous fluidization, in which distinguishable gas bubbles grow from the distributor, may coalesce with other bubbles and eventually burst at the surface of the bed. These bubbles intensify the mixing of solids and gases and bubble sizes tend to increase further with a rise in fluidization velocity. A slugging regime is observed when the bubble diameter increases up to the reactor diameter. In a turbulent regime, bubbles grow and start breaking up with the expansion of the bed. Under these conditions, the top surface of the bed is no longer distinguishable. In fast fluidization or pneumatic fluidization, particles are transported out of the bed and need to be recycled back into the reactor. No distinct bed surface is observed.

Fluidized bed reactors have the following advantages:

Uniform Particle Mixing: Due to the intrinsic fluid-like behavior of the solid particulate material, fluidized beds do not experience poor mixing as in packed beds. The elimination of radial and axial concentration gradients also allows for better fluid-solid contact, which is essential for reaction efficiency and quality.

Uniform Temperature Gradients: Many chemical reactions require the addition or removal of heat. Local hot or cold spots within the reaction bed are avoided in a fluidized situation.

Ability to Operate Reactor Continuously: The fluidized bed nature of these reactors allows for the ability to continuously withdraw the product(s) and introduce new reactants into the reaction vessel. On top of continuous operation of the chemical reactions, the fluidized bed allows also to continuously, or at a given frequency, withdraw solid material or add continuously or at a given frequency new fresh solid material thanks to the flowable solid particulate material.

Heat can be produced by passing an electrical current through a conducting material that has sufficiently high resistivity (the resistor) to transform electricity into heat. Electrical resistivity (also called specific electrical resistance or volume resistivity, is an intrinsic property independent of shape and size) and its inverse, electrical conductivity, is a fundamental property of a material that quantifies how strongly it resists or conducts electric current (SI unit of electrical resistivity is the ohm-meter ($\Omega \cdot m$) and for conductivity Siemens per meter (S/m)).

When electricity is passed through a fixed bed of electrically conducting particulate solids, having a sufficient resistivity, the bed offers resistance to the flow of current; this resistance depends on many parameters, including the nature of the solid, the nature of the linkages among the particles within the bed, the bed voidage, the bed height, the electrode geometry, etc. If the same fixed bed is fluidized by passing gas, the resistance of the bed increases; the resistance offered by the conducting particles generates heat within the bed and can maintain the bed in isothermal conditions (termed an electrothermal fluidized bed or electrofluid reactor). In many high-temperature reactions, electrofluid reactors offer in situ heating during the reaction and are particularly useful for operating endothermic reactions and hence save energy because no external heating or transfer of heat is required.

It is a prerequisite that at least part of the solid particulate material is electrically conducting but non-conducting solid particulates can be mixed and still result in enough heat generation. Such non-conducting or very high resistivity solids can play a catalytic role in the chemical conversion. The characteristics of the bed material determine the resistance of an electrothermal fluidized bed furnace; as this is a charge resistor type of heat generation, the specific resistivity of the particles affects the bed resistance. The size, shape, composition, and size distribution of the particles also influence the magnitude of the bed resistance. Also, when the bed is fluidized, the voids generated between the particles increases the bed resistance. The total resistance of the bed is the sum of two components, e.g. the electrode contact-resistance (i.e., the resistance between the electrode and the bed) and the bed resistance. A large contact-resistance will cause extensive local heating in the vicinity of the electrode while the rest of the bed stays rather cool.

The following factors determine the contact-resistance: current density, fluidization velocity, type of bed material, electrode size and the type of material used for the electrodes. The electrode compositions can be advantageously metallic like iron, cast iron or other steel alloys, copper or a copper-based alloy, nickel or a nickel-based alloy or refractory like metal, intermetallics or an alloy of Zr, Hf, V, Nb, Ta, Cr, Mo, W or ceramic-like carbides, nitrides or carbon-based like graphite. The area of contact between the bed material and the electrodes can be adjusted, depending on the electrode submergence and the amount of particulate material in the fluidized bed. Hence, the electrical resistance and the power level can be manipulated by adjusting these variables. Advantageously, to prevent overheating of the electrodes compared to the fluidised bed, the resistivity of the electrode should be lower (and hence the joule heating) than of the particulate material of the fluidized bed. In a preferred embodiment, the electrodes can be cooled by passing a colder fluid inside or outside the electrodes. Such fluids can be any liquid that vaporises upon a heating, gas stream or can be a part of the colder feedstock that first cools the electrode before entering the fluidised bed.

Bed resistance can be predicted by the ohmic law. The mechanism of current transfer in fluidized beds is believed to occur through current flow along continuous chains of conducting particles at low operating voltages. At high voltages, a current transfer occurs through a combination of chains of conducting particles and arcing between the electrode and the bed as well as particle-to-particle arcings that might ionize the gas, thereby bringing down the bed resistance. Arcing inside the bed, in principle, is not desirable as it would lower the electrical and thermal efficiency. The gas velocity impacts strongly the bed resistance, a sharp increase in resistance from the settled bed onward when the gas flow rate is increased; a maximum occurred close to the incipient fluidization velocity, followed by a decrease at higher velocities.

At gas flow rates sufficient to initiate slugging, the resistance again increased. Particle size and shape impact resistance as they influence the contacts points between particles. In general, the bed resistivity increases 2 to 5 times from a settled bed (e.g. 20 Ohm.cm for graphite) to the incipient fluidisation (60 Ohm.cm for graphite) and 10 to 40 times from a settled bed to twice (300 Ohm.cm for graphite) the incipient fluidisation velocity. Non or less-conducting particles can be added to conducting particles. If the conducting solid fraction is small, the resistivity of the bed would increase due to the breaking of the linkages in the chain of conducting solids between the electrodes. If the non-conducting solid fraction is finer in size, it would fill up the interstitial gaps or voidage of the larger conducting solids and hence increase the resistance of the bed.

In general, for a high desired heating power, a high current at a low voltage is preferred. The power source can be either AC or DC. Voltages applied in an electrothermal fluidized bed are typically below 100 V to reach enough heating power. The electrothermal fluidized bed can be controlled in the following three ways:

1. Adjusting the gas flow: Because the conductivity of the bed depends on the extent of voidage or gas bubbles inside the bed, any variation in the gas flow rate would change the power level; hence the temperature can be controlled by adjusting the fluidizing gas flow rate. The flow rate required for optimum performance corresponds to a velocity which equals or slightly exceeds the minimum fluidization velocity.

2. Adjusting the electrode submergence: The power level can also be controlled by varying the electrode immersion level inside the bed because the conductivity of the bed is dependent on the area of contact between the conducting particles and the electrode: the surface area of the electrode available for current flow increases with electrode submergence, leading to a reduction in overall resistance.

3. Adjusting the applied voltage: although changing the power level by using the first two methods is often more affordable or economical than increasing the applied voltage, however in electrothermal fluidized beds three variables are available to control the produced heating power.

The wall of the reactor is generally made of graphite, ceramics (like SiC), high-melting metals or alloys as it is versatile and compatible with many high-temperature reactions of industrial interest. The atmosphere for the reaction is often restricted to the neutral or the reducing type as an oxidising atmosphere can combust carbon materials or create a non-conducting metal oxide layer on top of metals or alloys. The wall and/or the distribution plate itself can act as an electrode for the reactor. The fluidized solids can be graphite, carbon, or any other high-melting-point, electrically conducting particles. The other electrodes, which is usually immersed in the bed, can also be graphite or a high-melting-point metal, intermetallics or alloys.

It may be advantaged to generate the required reaction heat by heating the conductive particles and/or catalyst particles in a separate zone of the reactor where little or substantially no feedstock hydrocarbons are present, but only diluent gases. The benefit is that the appropriate conditions of fluidization to generate heat by passing electrical current through a bed of conductive particles can be optimized whereas the optimal reaction conditions during hydrocarbon transformation can be selected for the other zone of the reactor. Such conditions of optimal void fraction and linear velocity might be different for heating purposes and chemical transformation purposes.

In an embodiment of the present disclosure, the installation comprises of two zones arranged in series namely a first zone being a heating zone and a second zone being a reaction zone, where the conductive particles and catalyst particles are continuously moved or transported from the first zone to the second zone and vice versa. The first and second zones can be different parts of a fluidized bed or can be located in separate fluidized beds reactors connected to each other.

In the said embodiment, the process to perform a catalytic cracking reaction of a hydrocarbon having at least four carbons, said process comprising the steps of:
a) providing at least one fluidized bed reactor comprising at least two electrodes and a bed comprising particles;
b) putting the particles in a fluidized state by passing upwardly through the said bed a fluid stream, to obtain a fluidized bed;
c) heating the fluidized bed to a temperature ranging from 500° C. to 850° C. to conduct the endothermic catalytic cracking reaction of a hydrocarbon having at least four carbons; and
d) optionally recovering the cracking products of the reaction;
wherein the particles of the bed comprise electrically conductive particles and particles of a catalytic composition, wherein at least 10 wt. % of the particles based on the total weight of the particles of the bed are electrically conductive particles and have a resistivity ranging from 0.001 Ohm.cm to 500 Ohm.cm at 500° C., wherein the at least one fluidized bed reactor provided in step a) comprises a heating zone and a reaction zone and wherein the fluid stream provided in step b) is provided to the heating zone and comprises diluent gases and the step c) of heating the fluidized bed to a temperature ranging from 500° C. to 850° C. to conduct the catalytic cracking reaction of a hydrocarbon having at least four carbons comprises the following sub-steps:
heating the fluidized bed to a temperature ranging from 500° C. to 850° C. by passing an electric current through the heating zone of the at least one fluidized bed,
transporting the heated particles from the heating zone to the reaction zone,
in the reaction zone, putting the heated particles in a fluidized state by passing upwardly through the said bed of the reaction zone a fluid stream comprising a hydrocarbon feedstock, and optional diluent gases to obtain a fluidized bed and to conduct the endothermic catalytic cracking reaction on the hydrocarbon having at least four carbons,
optionally, recovering the particles from the reaction zone and recycling them to the heating zone.

For example, the diluent gases can be one or more selected from steam, hydrogen, carbon dioxide, argon, helium, nitrogen and methane.

For example, the at least one fluidized bed reactor is at least two fluidized bed reactors connected one to each other wherein at least one of said at least two fluidized bed reactors is the heating zone and at least another of said at least two fluidized bed reactors is the reaction zone. With preference, the at least one fluidized bed reactor being the heating zone comprises gravitational or pneumatic transport means to transport the particles from the heating zone to the reaction zone and/or the installation comprises means arranged to inject a hydrocarbon feedstock to the at least one fluidized bed reactor being the reaction zone. The installation is devoid of means to inject a hydrocarbon feedstock to the at least one fluidized bed reactor being the heating zone.

For example, the at least one fluidized bed reactor is a single one fluidized bed reactor wherein the heating zone is the bottom part of the fluidized bed reactor while the reaction zone is the top part of the fluidised bed reactor. With preference, the installation comprises means to inject a hydrocarbon feedstock and/or diluent between the two zones. The diameter of the heating zone and reaction zone can be different to accomplish optimum conditions for heating in the bottom zone and optimum conditions for hydrocarbon conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone. The step c) provides that the catalytic cracking reaction is performed on a hydrocarbon feedstock and optionally steam which implies that a hydrocarbon feedstock and optionally steam are provided. It is understood that the hydrocarbon feedstock is provided to the reaction zone and that when the heating zone is separated from the reaction zone then, with preference, no hydrocarbon feedstock is provided to the heating zone. When the heating zone and the reaction zone are mixed (i.e. the same zone); the fluid stream provided in step b) comprises a hydrocarbon feedstock. The fluid stream may be a gaseous stream and/or a vaporized stream.

It is a specific embodiment of the present invention that the distance between the heat sources, being the hot particulate material and the feedstock is significantly reduced because of the small size of the particulates and the mixing of the particulates in the vaporous fluidising stream, compared to steam reformer tubes having typically 2.5 to 25 cm internal diameter requiring large temperature gradients to concur the large distance that heat has to travel.

In a preferred embodiment, the volumetric heat generation rate is greater than 0.1 MW/m$^3$ of fluidized bed, more preferably greater than 1 MW/m$^3$, in particular, greater than 3 MW/m$^3$.

The Bed Comprising Particles

According to the disclosure, the particles of the bed comprises electrically conductive particles and catalytic particles. For example, the catalytic particles are electrically conductive. For example, the electrically conductive particles are a mixture of catalytic particles and non-catalytic particles.

According to the disclosure the particles of the bed comprises at least 10 wt. % of electrically conductive particles based on the total weight of the particles of the bed.

For example, the content of electrically conductive particles based on the total weight of the bed is ranging from 10 wt. % to 100 wt. %; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %; and most preferably at least 30 wt. % or at least 40 wt. % or at least 50 wt. % or at least 60 wt. %.

For example, the content of electrically conductive particles based on the total weight of the bed is at most 75 wt. % based on the total weight of the particles of the bed; preferably, at most 80 wt. %, more preferably, at most 85 wt. %; even more preferably at most 90 wt. %; and most preferably at most 95 wt. % or at most 98 wt. % or is 100 wt. %.

To achieve the required temperature necessary to carry out the catalytic cracking reaction, at least 10 wt. % of the particles based on the total weight of the particles of the bed are electrically conductive and have a resistivity ranging from 0.001 Ohm.cm to 500 Ohm.cm at 500° C.

For example, the electrically conductive particles have a resistivity ranging from 0.005 to 400 Ohm.cm at 500° C., preferably ranging from 0.01 to 300 Ohm.cm at 500° C.; more preferably ranging from 0.05 to 150 Ohm.cm at 500° C. and most preferably ranging from 0.1 to 100 Ohm.cm at 500° C.

For example, the electrically conductive particles have a resistivity of at least 0.005 Ohm.cm at 500° C.; preferably of at least 0.01 Ohm.cm at 500° C., more preferably of at least 0.05 Ohm.cm at 500° C.; even more preferably of at least 0.1 Ohm.cm at 500° C., and most preferably of at least 0.5 Ohm.cm at 500° C.

For example, the electrically conductive particles have a resistivity of at most 400 Ohm.cm at 500° C.; preferably of at most 300 Ohm.cm at 500° C., more preferably of at most 200 Ohm.cm at 500° C.; even more preferably of at most 150 Ohm.cm at 500° C., and most preferably of at most 100 Ohm.cm at 500° C.

For example, the particles of the bed have an average particle size ranging from 5 to 300 µm as determined by sieving according to ASTM D4513-11, preferably ranging from 10 to 200 µm and more preferably ranging from 20 to 200 µm or from 30 to 150 µm.

For example, the electrically conductive particles of the bed have an average particle size ranging from 5 to 300 µm as determined by sieving according to ASTM D4513-11, preferably ranging from 10 to 200 µm and more preferably ranging from 20 to 200 µm or from 30 to 150 µm.

Determination by sieving according to ASTM D4513-11 is preferred. In case the particles have an average size of below 20 µm the determination of the average size can also be done by Laser Light Scattering according to ASTM D4464-15.

For example, the particles of a catalytic composition have an average particle size ranging from 5 to 300 µm as determined by sieving according to ASTM D4513-11, preferably ranging from 10 to 200 µm and more preferably ranging from 20 to 200 µm or from 30 to 150 µm.

The electrical resistance is measured by a four-probe DC method using an ohmmeter. A densified power sample is shaped in a cylindrical pellet that is placed between the probe electrodes. Resistivity is determined from the measured resistance value, R, by applying the known expression ρ=R×A/L, where L is the distance between the probe electrodes typically a few millimetres and A the electrode area.

The solid particulate material can exhibit electronic, ionic or mixed electronic-ionic conductivity. The ionic bonding of many refractory compounds allows for ionic diffusion and correspondingly, under the influence of an electric field and appropriate temperature conditions, ionic conduction.

The electrical conductivity, σ, the proportionality constant between the current density j and the electric field E, is given by $$\sigma j/E = \Sigma c_i \times Z_i q \times \mu_i$$

where $c_i$ is the carrier density (number=cm$^3$), $\mu_i$ the mobility (cm$^2$/Vs), and Z'q the charge (q=1.6×10$^{-19°}$ C.) of the ith charge carrier. The many orders of magnitude differences in between metals, semiconductors and insulators generally result from differences in c rather than µ. On the other hand, the higher conductivities of electronic versus ionic conductors are generally due to the much higher mobilities of electronic versus ionic species.

The most common materials that can be used for resistive heating can be subdivided into nine groups:

(1) Metallic alloys for temperatures up to 1200-1400° C.,
(2) non-metallic resistors like silicon carbide (SiC), molybdenum disilicide (MoSi$_2$) nickel silicide (NiSi), sodium silicide (Na$_2$Si), magnesium silicide (Mg$_2$Si), platinum silicide (PtSi), titanium silicide (TiSi$_2$) and tungsten silicide (WSi$_2$) up to 1600-1900° C.,
(3) several mixed oxides and/or mixed sulphides being doped with one or more lower-valent cation with variable temperature optima,
(4) carbons like graphite up to 2000° C.,
(5) metallic carbides,
(6) transition metal nitrides,
(7) metallic phosphides,
(8) superionic conductors and
(9) phosphate electrolytes.

A first group of metallic alloys, for temperatures up to 1150-1250° C., is constituted by Ni—Cr alloys with low Fe content (0.5-2.0%), preferably alloy Ni—Cr (80% Ni, 20% Cr) and (70 Ni, 30% Cr). Increasing the content of Cr increases the material resistance to oxidation at high temperatures. A second group of metallic alloys having three components are Fe—Ni—Cr alloys, with maximum operating temperature in an oxidizing atmosphere to 1050-1150° C. but which can be conveniently used in reducing atmospheres or Fe—Cr—Al (chemical composition 15-30% Cr, 2-6% Al and Fe balance) protecting against corrosion by a surface layer of oxides of Cr and Al, in oxidizing atmospheres can be used up to 1300-1400° C. Silicon carbide as non-metallic resistor can exhibit wide ranges of resistivity that can be controlled by the way they are synthesized and the presence of impurities like aluminium, iron, oxide, nitrogen or extra carbon or silicon resulting in non-stoichiometric silicon carbide. In general silicon carbide has a high resistivity at low temperature but has good resistivity in the range of 500 to 1200° C. In an alternative embodiment, the non-metallic resistor can be devoid of silicon carbide, and/or can comprise molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

Graphite and amorphous carbon (like coke, petroleum coke, and/or carbon black) have rather low resistivity values, with a negative temperature coefficient up to about 600° C. after which the resistivity starts to increase.

Many mixed oxides being doped with one or more lower-valent cations, having in general too high resistivity at low temperature, become ionic or mixed conductors at high temperature. The following circumstances can make oxides sufficient conductors for heating purposes: ionic conduction in solids is described in terms of the creation and motion of atomic defects, notably vacancies and interstitials of which its creation and mobility is very positively dependent on temperature. Such mixed oxides are ionic conductors, namely being doped with one or more lower-valent cations. Three mechanisms for ionic defect formation in oxides are known: (1) Thermally induced intrinsic ionic disorder (such as Schottky and Frenkel defect pairs resulting in non-stoichiometry), (2). Redox-induced defects and (3) Impurity-induced defects. The first two categories of defects are predicted from statistical thermodynamics and the latter form to satisfy electroneutrality. In the latter case, high charge carrier densities can be induced by substituting lower valent cations for the host cations. Mixed oxides and/or mixed sulphides with fluorite, pyrochlore or perovskite structure are very suitable for substitution by one or more lower-valent cations.

Several sublattice disordered oxides or sulphides have high ion transport ability at increasing temperature. These are superionic conductors, such as $LiAlSiO_4$, $Li_{10}GeP_2S_{12}$, $Li_{3.6}Si_{0.6}P_{0.4}$, NaSICON (sodium (Na) Super Ionic CONductor) with the general formula $Na_{1+x}Zr_2P_{3-x}Si_xO_{12}$ with $0<x<3$, for example $Na_3Zr_2PSi_2O_{12}$ (x=2), or sodium beta alumina, such as $NaAl_{11}O_{17}$, $Na_{1-6}Al_{11}O_{17.3}$, and $Na_{1.76}Li_{0.38}Al_{10.62}O_{17}$.

High concentrations of ionic carriers can be induced in intrinsically insulating solids and creating high defective solids. Thus, the electrically conductive particles of the bed are or comprise one or more mixed oxides being ionic conductors, namely being doped with one or more lower-valent cations. With preference, the mixed oxides are selected from one or more oxides having a cubic fluorite structure being at least partially substituted with one or more lower-valent cations, preferentially selected from Sm, Gd, Y, Sc, Yb, Mg, Ca, La, Dy, Er, Eu; and/or from one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABO_3$-perovskites with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2O_7$-pyrochlores with A trivalent cation and B tetra-valent cation being at least partially substituted in A position with one or more lower-valent cations, preferentially selected from Ca or Mg, and comprising at least one of Sn, Zr and Ti in B position.

With preference, the one or more mixed sulphides are selected from one or more sulphides having a cubic fluorite structure being at least partially substituted with one or more lower-valent cations, preferentially selected from Sm, Gd, Y, Sc, Yb, Mg, Ca, La, Dy, Er, Eu; and/or from one or more $ABS_3$ structures with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABS_3$ structures with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2S_7$ structures with A trivalent cation and B tetra-valent cation being at least partially substituted in A position with one or more lower-valent cations, preferentially selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

Said one or more oxides having a cubic fluorite structure, said one or more $ABO_3$-perovskites with A and B tri-valent cations, said one or more $ABO_3$-perovskites with A bivalent cation and B tetra-valent cation or said one or more $A_2B_2O_7$- pyrochlores with A trivalent cation and B tetra-valent cation being at least partially substituted with lower valent cations, said one or more sulphides having a cubic fluorite structure, said one or more $ABS_3$ structures with A and B tri-valent cations, said one or more $ABS_3$ structures with A bivalent cation and B tetra-valent cation, said one or more $A_2B_2S_7$ structures with A trivalent cation and B tetra-valent cation being at least partially substituted with lower valent cations also means that the same element, being a high-valent cation, can be reduced in the lower-valent equivalent, for example, Ti(IV) can be reduced in Ti(III) and/or Co(III) can be reduced in Co(II) and/or Fe(III) can be reduced in Fe(II) and/or Cu(II) can be reduced in Cu(I).

Phosphate electrolytes such as $LiPO_4$ or $LaPO_4$ can also be used as electrically conductive particles.

Metallic carbides, transition metal nitrides and metallic phosphides can also be selected as electrically conductive particles. For example, metallic carbides are selected from iron carbide ($Fe_3C$), molybdenum carbide (mixture of MoC and $Mo_2C$). For example, said one or more transition metal nitrides are selected from zirconium nitride (ZrN), tungsten nitride (mixture of $W_2N$, WN, and $WN_2$), vanadium nitride (VN), tantalum nitride (TaN), and/or niobium nitride (NbN). For example, said one or more metallic phosphides are selected from copper phosphide ($Cu_3P$), indium phosphide (InP), gallium phosphide (GaP), sodium phosphide $Na_3P$), aluminium phopshide (AlP), zinc phosphide ($Zn_3P_2$) and/or calcium phosphide ($Ca_3P_2$).

For example, the electrically conductive particles of the bed are or comprise silicon carbide. For example, at least 10 wt. % of the electrically conductive particles based on the total weight of the particles of the bed are silicon carbide particles and have a resistivity ranging from 0.001 Ohm.cm to 500 Ohm.cm at of 500° C.

In the embodiment wherein the electrically conductive particles of the bed are or comprise silicon carbide, the person skilled in the art will have the advantage to conduct a step of pre-heating with a gaseous stream said fluidized bed reactor before conducting said endothermic reaction in the fluidized bed reactor. Advantageously, the gaseous stream is a stream of inert gas, i.e., nitrogen, argon, helium, methane, carbon dioxide, hydrogen, and/or steam. The temperature of the gaseous stream can be at least 500° C., or at least 550° C., or at least 600° C., or at least 650° C., or at least 700° C. Advantageously, the temperature of the gaseous stream can be comprised between 500° C. and 900° C., for example between 600° C. and 800° C. or between 650° C. and 750° C. Said gaseous stream of inert gas can also be used as the fluidification gas. The pre-heating of the said gaseous stream of inert gas is performed thanks to conventional means, including using electrical energy. The temperature of the gaseous stream used for the preheating of the bed doesn't need to reach the temperature reaction.

Indeed, the resistivity of silicon carbide at ambient temperature is high, to ease the starting of the reaction, it may be useful to heat the fluidized bed by external means, as with preference the fluidized bed reactor is devoid of heating means. Once the bed is heated at the desired temperature, the use of a hot gaseous stream may not be necessary.

However, in an embodiment, the electrically conductive particles of the bed are or comprise a mixture of silicon carbide particles and electrically conductive particles different from silicon carbide particles.

The pre-heating step may be also used in the case wherein electrically conductive particles different from silicon carbide particles are present in the bed. For example, it may be used when the content of silicon carbide in the electrically conductive particles of the bed is more than 80 wt. % based on the total weight of the electrically conductive particles of the bed, for example, more than 85 wt. %, for example, more than 90 wt. %, for example, more than 95 wt. %, for example, more than 98 wt. %, for example, more than 99 wt. %. However, a pre-heating step may be used whatever is the content of silicon carbide particles in the bed.

In the embodiment wherein the electrically conductive particles of the bed are or comprise a mixture of silicon carbide particles and electrically conductive particles different from silicon carbide particles, the electrically conductive particles of the bed may comprise from 10 wt. % to 99 wt. % of silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of silicon carbide particles and electrically conductive particles different from silicon carbide particles and the electrically conductive particles of the bed comprises at least 40 wt. % of silicon carbide particles based on the total weight of the electrically conductive particles of the bed; preferably at least 50 wt. %, more preferably at least 60 wt. %, even more preferably at least 70 wt. % and most preferably at least 80 wt. %.

In an embodiment, the electrically conductive particles of the bed may comprise from 10 wt. % to 90 wt. % of electrically conductive particles different from silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

However, it may be interesting to keep the content of electrically conductive particles different from silicon carbide particles quite low in the mixture. Thus, in an embodiment, the electrically conductive particles of the bed are or comprise a mixture of silicon carbide particles and electrically conductive particles different from silicon carbide particles and electrically conductive particles of the bed comprises from 1 wt. % to 20 wt. % of electrically conductive particles different from silicon carbide based on the total weight of the electrically conductive particles of the bed; preferably, from 2 wt. % to 15 wt. %, more preferably, from 3 wt. % to 10 wt. %, and even more preferably, from 4 wt. % to 8 wt. %.

For example, the electrically conductive particles of the bed are or comprise a mixture of silicon carbide particles and electrically conductive particles different from silicon carbide particles and the said electrically conductive particles different from silicon carbide particles are particles selected from graphite, carbon black, coke, petroleum coke and/or any mixture thereof. For example, the said electrically conductive particles different from silicon carbide particles are or comprise graphite.

In an embodiment, from 50 wt. % to 100 wt. % of the electrically conductive particles of the bed based on the total weight of the electrically conductive particles of the bed area mixture of silicon carbide particles and electrically conductive particles different from silicon carbide particles and the said electrically conductive particles different from silicon carbide particles are particles selected from graphite, carbon black, coke, petroleum coke and/or any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

Thus, in an embodiment, the electrically conductive particles are a combination of silicon carbide particles and graphite particles. Such electrically conductive particles, upon the electrification of the fluidized bed reactor, will heat up and because of their fluidification, will contribute to the raise and/or to the maintaining of the temperature within the reactor. The Joule heating of such electrically conductive material allows accelerating the heating of the reactant and/or of the catalyst that is present within the fluidized bed reactor.

When graphite is selected, it can preferably be flake graphite. It is also preferable that the graphite has an average particle size ranging from 1 to 400 μm as determined by sieving according to ASTM D4513-11, preferably from 5 to 300 μm, more preferably ranging from 10 to 200 μm and most preferably ranging from 20 to 200 μm or from 30 to 150 μm.

The presence of electrically conductive particles different from silicon carbide particles in the bed allows applying the process according to the disclosure with or without the pre-heating step, preferably without the pre-heating step. Indeed, the electrically conductive particles, upon the electrification of the fluidized bed reactor, will heat up and because of their fluidification, will contribute to raising and/or maintaining the desired temperature within the reactor.

The Silicon Carbide Particles

For example, the silicon carbide is selected from sintered silicon carbide, nitride-bounded silicon carbide, recrystallised silicon carbide, reaction bonded silicon carbide and any mixture thereof.

Sintered SiC (SSiC) is a self-bonded material containing a sintering aid (typically boron) of less than 1% by weight.

Recrystallized silicon carbide (RSiC), a high purity SiC material sintered by the process of evaporation—condensation without any additives.

Nitride-bonded silicon carbide (NBSC) is made by adding fine silicon powder with silicon carbide particles or eventually in the presence of a mineral additive and sintering in a nitrogen furnace. The silicon carbide is bonded by the silicon nitride phase ($Si_3N_4$) formed during nitriding.

Reaction bonded silicon carbide (RBSC), also known as siliconized silicon carbide or SiSiC, is a type of silicon carbide that is manufactured by a chemical reaction between porous carbon or graphite with molten silicon. The silicon reacts with the carbon forming silicon carbide and bonds the silicon carbide particles. Any excess silicon fills the remaining pores in the body and produces a dense SiC—Si composite. Due to the left-over traces of silicon, reaction bonded silicon carbide is often referred to as siliconized silicon carbide. The process is known variously as reaction bonding, reaction sintering, self-bonding, or melt infiltration.

In general, high purity SiC particles have a resistivity above 1000 Ohm.cm, whereas sintered, reaction bonded and nitride-bonded can exhibit resistivities of about 100 to 1000 depending on the impurities in the SiC phase. Electrical resistivity of bulk polycrystalline SiC ceramics shows a wide range of resistivity depending on the sintering additive and heat-treatment conditions (Journal of the European Ceramic Society, Volume 35, Issue 15, December 2015, Pages 4137; Ceramics International, Volume 46, Issue 4, March 2020, Pages 5454). SiC polytypes with high purity possess high electrical resistivity ($>10^6 \Omega.cm$) because of their large bandgap energies. However, the electrical resistivity of SiC is affected by doping impurities. N and P act as n-type dopants and decrease the resistivity of SiC, whereas Al, B, Ga, and Sc act as p-type dopants. SiC doped with Be, O, and V are highly insulating. N is considered the most efficient dopant for improving the electrical conductivity of SiC. For N doping of SiC (to decrease resistivity) $Y_2O_3$ and $Y_2O_3$—$REM_2O_3$ (REM=rare earth metal=Sm, Gd, Lu) have been used as sintering additives for the efficient growth of conductive SiC grains containing N donors. N-doping in SiC grains was promoted by the addition of nitrides (AlN, BN, $Si_3N_4$, TiN, and ZrN) or combinations of nitrides and $REEM_2O_3$ (AlN— $REM_2O_3$ (REM=Sc, Nd, Eu, Gd, Ho, and Er) or TiN—$Y_2O_3$).

It is a preferred embodiment of the present invention to withdraw continuously or intermittently solid particulate material and particulate catalyst, containing carbonaceous depositions, from the electrothermal fluidised bed vessel, transporting it to a fluidised bed regeneration vessel, burning the carbonaceous depositions with a stream containing oxygen and optionally carbon dioxide, transporting the at least partially regenerated solid particulate material and particulate catalyst back into the electrothermal fluidised bed reformer vessel.

It is a preferred embodiment of the present invention to recover the sensible and latent heat in the reactor effluent product to preheat the feedstock (both the hydrocarbons, hydrogen and/or steam).

The Catalytic Composition

For example, the content of the particles of a catalytic composition based on the total weight of the particles of the bed is ranging from 30 wt. % to 100 wt. %; preferably from 32 wt. % to 95 wt. %, more preferably from 35 wt. % to 90 wt. %, even more preferably from 37 wt. % to 85 wt. %, most preferably from 40 wt. % to 80 wt. %, even most preferably from 45 wt. % to 75 wt. % or from 50 wt. % to 70 wt. %. In the case where the content of the particles of a catalytic composition based on the total weight of the particles of the bed is 100 wt. %, at least a part of said particles of a catalytic composition are also electrically conductive particles For example, the particles of a catalytic composition have an average particle size ranging from 5 to 300 μm as determined by sieving according to ASTM D4513-11, preferably ranging from 10 to 200 μm and more preferably ranging from 30 to 150 μm.

For example, the catalyst composition comprises (values are on dry final catalyst composition basis, balance to 100 wt. % being a binder) from 5.0 to 90.0 wt. % of one or more zeolites comprising at least one 10-membered ring channel and based on the total weight of the catalyst composition, preferably from 10.0 to 85.0 wt. %, more preferably from 20.0 to 80.0 wt. % and/or from 5.0 to 90.0 wt. % of one or more zeolites comprising pores with a diameter of at least 0.5 nm as determined by argon adsorption and based on the total weight of the catalyst composition, preferably from 10.0 to 85.0 wt. %, more preferably from 20.0 to 80.0 wt. %. With preference, said one or more zeolites comprise between at least one 10-membered ring channel and at least one 12-membered ring channel and/or comprise pore with a diameter between 0.5 nm and 1.5 nm, preferably between 0.52 nm and 0.95 nm, more preferably between 0.7 nm and 0.9 nm;

For example, the catalyst composition comprises a binder. With preference, said binder is one selected of silica, clays, such as clays from the kaolin family or clays from montmorillonite family and/or metal oxides, such as alumina.

It is advantageous that said one or more zeolites have a Si/Al molar ratio comprised between and 5000, preferably between 50 and 4000, more preferably between 120 and 2000.

It is also preferred that said one or more zeolites comprise from 0.01 to 10 wt. % of phosphorus based on the total weight content of the one or more zeolites, preferably from 0.1 wt. % to 8.0 wt. %. The modification of zeolites with phosphorous is known per se. This modification is carried out by treating zeolites with P-compounds in aqueous or non-aqueous media, by chemical vapor deposition of organic P-compounds or impregnation. The catalyst can be pre-formulated with binder or not. The preferred P-compounds used typically for this purpose can be selected from the group of phosphoric acid, $NH_4H_2PO_4$ or $(NH_4)_2HPO_4$.

The zeolites can comprise one or more metal compounds (M-comprising compound). The M-containing compound can be selected from organic compounds, salts, hydroxides and oxides. These compounds may also contain phosphorus. These compounds must be present in solubilized form, before bringing them into contact with the zeolite or by forming a solution when in contact with the zeolite.

Advantageously, the one or more metal compounds (M-comprising compounds) are selected from group-11 elements (i.e. of group IB elements according to CAS system, group-11 elements being in accordance with new IUPAC system), group-4 elements (i.e. of group IVB elements according to CAS system, group-4 elements being in accordance with the new IUPAC system), group-2 elements (i.e. of group IIA elements according to CAS system, group-2 elements being in accordance with the new IUPAC system), one or more elements selected from Ce, Sn, Co, Mo, Mn, Ni, Fe, Cr, Pt, Pd, In, Ga, Re, W and V and/or one or more rare earth elements. For reference, the above-mentioned new IUPAC system is described in *Pure & Appl. Chem.*, 1988, 60(3), 431-436.

With preference, the one or more metal compounds selected from group-11 elements are Ag, Au and/or Cu; and/or the one or more metal compounds selected from group-11 elements are in an amount ranging from 0.01 to 4.0 wt. % based on the total weight content of said one or more zeolites, more preferably from 0.1 to 3.5 wt. %, even more preferably from 1.0 to 3.0 wt. %.

With preference, the one or more metal compounds selected from group-4 elements are Ti and/or Zr; and/or the one or more metal compounds selected from group-4 elements are in an amount ranging from 0.5 to 10.0 wt. % based on the total weight content of said one or more zeolites, more preferably from 1.0 to 8.0 wt. %, even more preferably from 1.5 to 5.0 wt. %.

With preference, the one or more metal compounds selected from group-2 elements are Mg, Ca, Sr, and/or Ba; and/or the one or more metal compounds selected from group-2 elements are in an amount ranging from 0.1 to 5.0 wt. % based on the total weight content of said one or more zeolites, more preferably from 1.0 to 4.0 wt. %, even more preferably from 1.5 to 3.5 wt. %.

With preference, the one or more elements selected from Ce, Sn, Co, Mo, Mn, Ni, Fe, Cr, Pt, Pd, In, Ga, Re, W and V are in an amount ranging from 0.005 to 5.0 wt. % based on the total weight content of said one or more zeolites, more preferably from 0.01 to 4.5 wt. %, even more preferably from 0.1 to 4.0 wt. %.

With preference, the one or more rare earth elements are selected from Dy, La, Pm, Sm, Sc, Yb and/or Y; and/or the one or more metal compounds selected from the one or more rare earth elements are in an amount ranging from 0.1 to 15.0 wt. % based on the total weight content of said one or more zeolites, more preferably from 1.0 to 10.0 wt. %, even more preferably from 1.5 to 8.0 wt. %.

A preferred zeolite from the above-mentioned zeolites is a "medium pore size Zeolite" which is a zeolite having a pore size of from 0.5 to 0.65 nm as determined by argon adsorption, meaning a zeolite which has a pore size between the pore size of the small pore size zeolite (such as an A-type zeolite) and the pore size of the large pore size zeolite (such as a mordenite, an X-type zeolite and a Y-type zeolite), i.e., a zeolite comprising at least one 10-membered ring channel in the crystal framework thereof.

For example, the one or more zeolites are selected from the list comprising MFI, MEL, MTW, MTT and/or FER families, preferably from MFI, MEL and/or FER families. The one or more zeolites can also be selected among ZSM-8, ZSM-21 and/or ZSM-38, preferably among ZSM-8 and/or ZSM-38.

When the zeolite is selected from the MFI family, the zeolite is or comprises ZSM-5.

When the zeolite is selected from the MEL family, the zeolite is or comprises ZSM-11.

When the zeolite is selected from the MTW family, the zeolite is or comprises ZSM-12.

When the zeolite is selected from the MTT family, the zeolite is or comprises ZSM-23.

When the zeolite is selected from the FER family, the zeolite is or comprises ZSM-35.

Advantageously, the catalyst composition further comprises a catalyst support. With preference, said catalyst support is selected from the group comprising alumina, alumina sol, titania, zirconia, quartz, silica, silica sol, silica-alumina, silica-magnesia, silica-zirconia, silica-thoria, silica-beryllia, silica-titania, calcium-alumina, calcium-silicate, ceria-zirconia-alumina, ceria-titania-alumina, ceria-magnesia-alumina, calcium-silica-alumina, silica-alumina-zirconia, hafnia, lanthania, magnesia, ceria, zirconia stabilized with magnesia, zirconia stabilized with lanthania, zirconia stabilized with yttria, zirconia stabilized with ceria, alumina stabilized with lanthania, metal-aluminates, and mixture thereof. Example of metal aluminates are calcium aluminate and magnesium aluminate. Example of alumina are γ-alumina, δ-alumina, θ-alumina, and α-alumina. More preferably, said catalyst support is selected from alumina, alumina stabilized with lanthania, ceria-zirconia-alumina, ceria-titania-alumina and ceria-magnesia-alumina. Preferred support materials are those common materials (mentioned above) that can be used for resistive heating at the same time and which can be subdivided into metallic alloys and non-metallic resistors like silicon carbide (SiC) and molybdenum disilicide ($MoSi_2$), several mixed oxides with variable temperature optima and carbons like graphite. This latter option results in intimate contact between the catalytic active metal and the resistor particulate material.

With preference, said one or more zeolites are steamed, calcined, ion-exchanged, treated with acid solution and/or dealuminated. Said zeolite before modification with M and P, can be calcined, steamed, ion-exchanged, treated with an acid solution or it may undergo other treatments leading to dealumination. Dealumination of the zeolite can be performed simultaneously with the phosphorous modification.

Said catalytic composition can be further modified by ion exchange, calcination or steaming. If desired, to further improve the resistance of said one or more zeolites to the coking deactivation, before the contact with the hydrocarbon feedstock, said one or more zeolites can be subjected to heat treatment at 500° C. or more in the presence of steam.

Preferably, this heat treatment (steaming) is conducted at 500° C. to 900° C. and/or under a steam partial pressure of 0.01 MPa or more. The above-mentioned heat treatment can be conducted before a group IB metal is incorporated into the one or more zeolites, but it is preferred that the heat treatment is conducted after a group IB metal is incorporated into the one or more zeolites.

In a particular embodiment, the one or more zeolites can be combined with other materials that provide additional hardness, attrition resistance or catalytic activity to the finished catalyst product. Materials, which can be blended with the one or more zeolites, can be various inert or catalytically active matrix materials and/or various binder materials. Such materials include clays, silica and/or metal oxides such as alumina.

According to another embodiment, non-modified zeolite was first formulated with a binder and matrix materials and then modified with phosphorous and metals.

According to a particular embodiment, zeolites was optionally dealuminated and then modified with phosphorous during the formulation step. The introduction of the metal can be performed during the formulation step or on the formulated solid.

According to a preferred embodiment, zeolites was first optionally dealuminated and modified with phosphorous and then formulated. Introduction of the metal is performed simultaneously with a modification with phosphorous step or/and on formulated catalyst.

The catalyst composite may also optionally comprise binder and/or matrix material and/or metal phosphate. Preferably, the amount of zeolite, which is contained in the final catalyst composite can range from 10 to 90% by weight of the total catalyst composite, more preferably from 20 to 70% by weight.

Naturally occurring clays, which can be used as a binder, are for example clays from the kaolin family or montmorillonite family. Such clays can be used in the raw state as mined or they can be subjected to various treatments before use, such as calcination, acid treatment or chemical modification.

These components are effective in increasing the density of the catalyst and increasing the strength of the formulated catalyst. The catalyst may be formulated into spray-dried particles. Generally, the size of the catalyst particles can vary from about 20 to 300 µm. In general, spray-dried particles are used in fluidised bed reactors and exhibit a particle size of from about to 300 µm.

The crystal size of the zeolite contained in the catalyst composite, is preferably less than about 10 µm, more preferably less than about 5 µm and most preferably less than about 4 µm. The amount of zeolite, which is contained in the final catalyst composite ranges from 10 to 90% by weight of the total catalyst composite, preferably 20 to 70% by weight.

The formulated catalyst composite may undergo further treatments including further steaming, leaching, washing, drying, calcination, impregnations and ion exchanging steps.

The Installation

The terms "bottom" and "top" are to be understood in relation to the general orientation of the installation or the fluidized bed reactor. Thus, "bottom" will mean greater ground proximity than "top" along the vertical axis. In the different figures, the same references designate identical or similar elements.

FIG. 1 illustrates a prior art fluidized bed reactor 1 comprising a reactor vessel 3, a bottom fluid nozzle 5 for the introduction of a fluidizing gas and a hydrocarbon feedstock, an optional inlet 7 for the material loading, an optional outlet 9 for the material discharge and a gas outlet 11 and a bed 15. In the fluidized bed reactor 1 of FIG. 1 the heat is provided by preheating the feedstock by combustion of fossil fuels using heating means 17 arranged for example at the level of the line that provides the reactor with the fluidizing gas and the hydrocarbon feedstock.

The installation of the present disclosure is now described with reference to FIGS. 2 to 5. For sake of simplicity, internal devices are known by the person in the art that are used in fluidized bed reactors, like bubble breakers, deflectors, particle termination devices, cyclones, ceramic wall coatings, thermocouples, etc. . . . are not shown in the illustrations.

Figure 2:
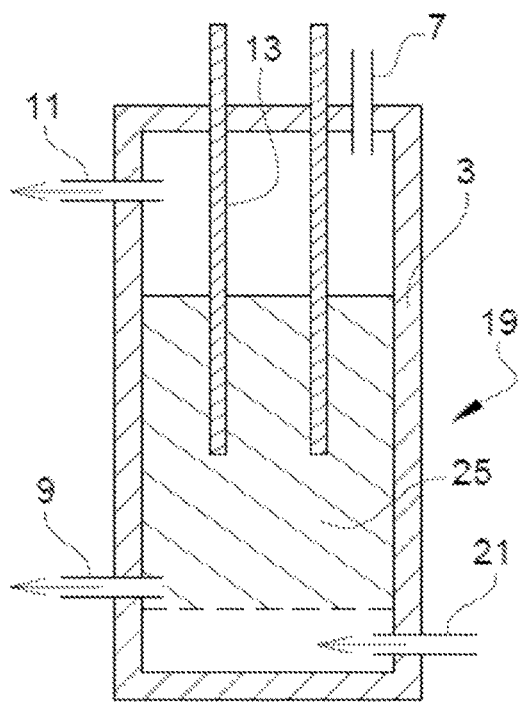
FIG. 2 illustrates an installation according to the disclosure with one reactor wherein the heating zone and reaction zone are the same.

FIG. 2 illustrates a first installation with a fluidized bed reactor 19 where the heating and reaction zone are the same. The fluidized bed reactor 19 comprises a reactor vessel 3, a bottom fluid nozzle 21 for the introduction of a fluidizing gas and a hydrocarbon feedstock, an optional inlet 7 for the material loading, an optional outlet 9 for the material discharge and a gas outlet 11. The fluidized bed reactor 1 of FIG. 19 shows two electrodes 13 submerged in the bed 25.

Figure 3:
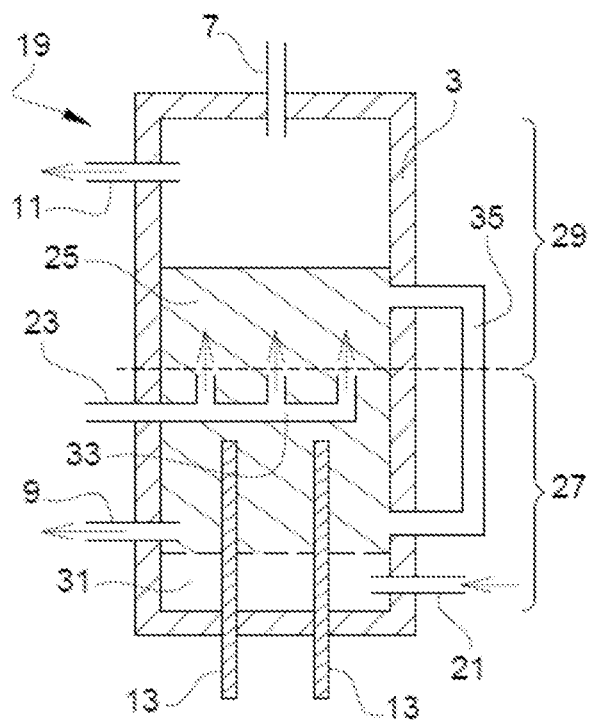
FIG. 3 illustrates an installation according to the disclosure with one reactor wherein the heating zone and reaction zone are arranged one above the other.

FIG. 3 illustrates an embodiment wherein at least one fluidized bed reactor 19 comprises a heating zone 27 and a reaction zone 29 with the heating zone 27 is the bottom zone and the reaction zone 29 is on top of the heating zone 27. One or more fluid nozzles 23 to provide a hydrocarbon feedstock to the reaction zone from a distributor 33. As it can be seen in FIG. 3, the one or more fluid nozzles 23 can be connected to a distributor 33 to distribute the hydrocarbon feedstock inside the bed 25.

Figure 4:
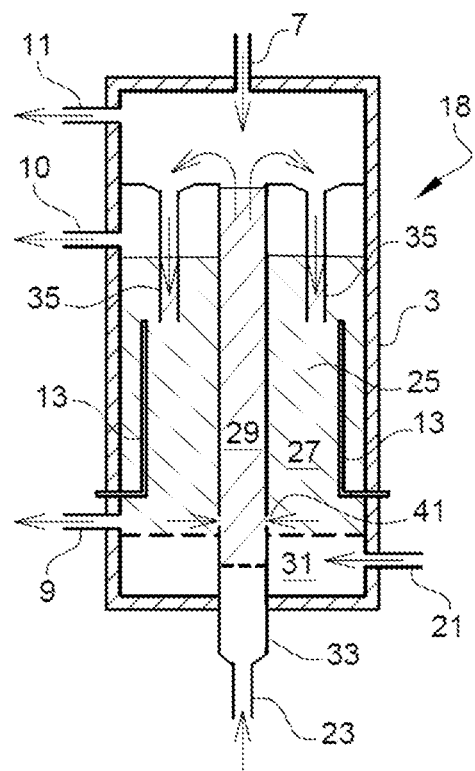
FIG. 4 illustrates an installation according to the disclosure with one reactor wherein the heating zone and reaction zone are arranged one lateral to the other.

FIG. 4 illustrates an installation wherein at least one fluidized bed reactor 18 comprises at least two lateral zones with the outer zone being the heating zone 27 and the inner zone being the reaction zone 29. The heated particles of the bed 25 from the outer zone are transferred to the inner zone by one or more openings 41 and mixed with the hydrocarbon feedstock and optionally steam. At the end of the reaction zone, the particles are separated from the reaction product and transferred to the heating zone.

Figure 5:
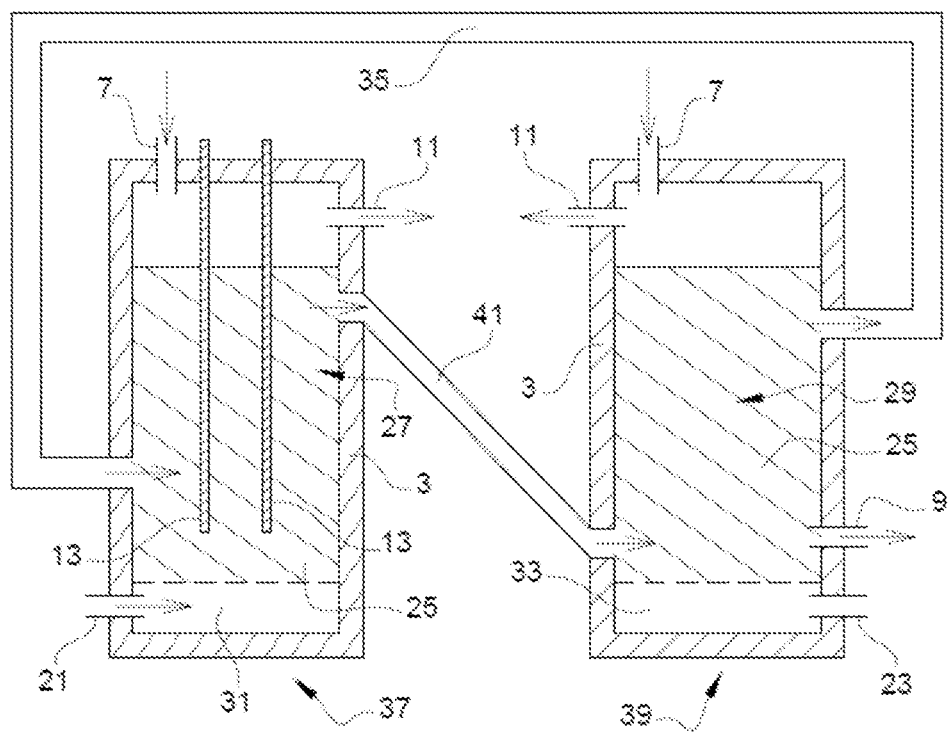
FIG. 5 illustrates an installation according to the disclosure with two reactors.

FIG. 5 illustrates the installation that comprises at least two fluidized bed reactors (37, 39) connected one to each other wherein at least one fluidized bed reactor is the heating zone 27 and one at least one fluidized bed reactor is the reaction zone 29.

The present disclosure provides for an installation to be used in a process to perform catalytic cracking reaction on one or more hydrocarbons having at least four carbons, according to the first aspect, said installation comprising at least one fluidized bed reactor (18, 19, 3, 39) comprising:
at least two electrodes 13
a reactor vessel 3;
one or more fluid nozzles (21; 23) for the introduction of a fluidizing gas and/or of a reaction stream within at least one fluidized bed reactor; and
a bed 25 comprising particles;
the fluidized bed reactor is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm.cm to 500 Ohm.cm at 500° C.

For example, one electrode is a submerged central electrode or two electrodes 13 are submerged within the reactor vessel 3 of at least one reactor (18, 19, 37).

For example, all the fluidized bed reactors are devoid of heating means. When stating that at least one of the fluidized bed reactors is devoid of "heating means", it refers to "classical" heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the fluidizing gas is one or more diluent gases. For example, the reaction stream comprises a hydrocarbon feedstock, in which the hydrocarbons of the hydrocarbon feedstock have at least four carbons, and optionally steam.

For example, the reactor vessel 3 has an inner diameter of at least 100 cm, or at least 200 cm; or at least 400 cm. Such a large diameter allows to carry out the chemical reaction at an industrial scale, for example at a weight hourly space velocity of said reaction stream comprised between 0.1 $h^{-1}$ and 100 $h^{-1}$, preferably comprised between 1.0 $h^{-1}$ and 50 $h^{-1}$, more preferably comprised between 1.5 $h^{-1}$ and 10 $h^{-1}$, even more preferably comprised between 2.0 $h^{-1}$ and 6.0 $h^{-1}$. The weight hourly space velocity is defined as the ratio of mass flow of the reaction stream to the mass of solid particulate material in the fluidized bed.

The at least one fluidized bed reactor (18, 19, 37) comprises at least two electrodes 13. One electrode is in electrical connection with the outer wall of the fluidized bed reactor, while one additional electrode is submerged into the fluidized bed 25, or both electrodes 13 are submerged into the fluidized bed 25. Said at least two electrodes 13 are electrically connected and can be connected to a power supply (not shown). It is advantageous that said at least two electrodes 13 are made of carbon-containing material. The person skilled in the art will have an advantage that the electrodes 13 are more conductive than the particle bed 25.

For example, at least one electrode 13 is made of or comprises graphite; preferably, all or the two electrodes 13 are made of graphite. For example, one of the electrodes is the reactor vessel, so that the reactor comprises two electrodes, one being the submerged central electrode and one being the reactor vessel 3.

For example, at least one fluidized bed reactor comprises at least one cooling device arranged to cool at least one electrode.

During use of the at least one fluidized bed reactor, an electric potential of at most 300 V is applied, preferably at most 250 V, more preferably at most 200 V, even more preferably at most 150 V, most preferably at most 100 V, even most preferably at most 90 V, or at most 80 V.

Thanks to the fact that the power of the electric current can be tuned, it is easy to adjust the temperature within the reactor bed.

The reactor vessel 3 can be made of graphite. In an embodiment, it can be made of electro-resistive material that is silicon carbide or a mixture of silicon carbide and one or more electrically conductive materials.

With preference, the reactor vessel 3 comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ). SiAlON ceramics are ceramics based on the elements silicon (Si), aluminium (Al), oxygen (O) and nitrogen (N). They are solid solutions of silicon nitride ($Si_3N_4$), where Si—N bonds are partly replaced with Al—N and Al—O bonds.

For example, the reactor vessel 3 is made of an electro-resistive material that is a mixture of silicon carbide and one or more electrically conductive materials; and the electro-resistive material of the reactor vessel 3 comprises from 10 wt. % to 99 wt. % of silicon carbide based on the total weight of the electro-resistive material; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the reactor vessel 3 is made of an electro-resistive material that is a mixture of silicon carbide and one or more carbon-containing materials; and the one or more carbon-containing materials are selected from graphite, carbon black, coke, petroleum coke and/or any mixture thereof; with preference, the carbon-containing material is or comprises graphite.

For example, the reactor vessel 3 is not conductive. For example, the reactor vessel 3 is made of ceramic.

For example, the at least one fluidized bed reactor (18, 19, 37, 39) comprises a heating zone 27 and a reaction zone 29, one or more fluid nozzles 21 to provide a fluidizing gas to at least the heating zone from a distributor 31, one or more fluid nozzles 23 to provide a hydrocarbon feedstock to the reaction zone, and means 41 to transport the particles from the heating zone 27 to the reaction zone 29 when necessary, and optional means 35 to transport the particles from the reaction zone 29 back to the heating zone 27.

For example, as illustrated in FIG. 3, the at least one fluidized bed reactor is a single one fluidized bed reactor 19 wherein the heating zone 27 is the bottom part of the fluidized bed reactor 19 while the reaction zone 29 is the top part of the fluidised bed reactor 19; with preference, the installation comprises one or more fluid nozzles 23 to inject a hydrocarbon feedstock between the two zones (27, 29) or in the reaction zone 29. The fluidized bed reactor 19 further comprises optionally an inlet 7 for the material loading, optionally an outlet 9 for the material discharge and a gas outlet 11. With preference, the fluidized bed reactor 19 is devoid of heating means. For example, the electrodes 13 are arranged at the bottom part of the fluidized bed reactor 19, i.e. in the heating zone 27. For example, the top part of the fluidised bed reactor 19, i.e. the reaction zone 29, is devoid of electrodes. Optionally, the fluidized bed reactor 19 comprises means 35 to transport the particles from the reaction zone 29 back to the heating zone 27; such as by means of a line arranged between the top part and the bottom part of the fluidized bed reactor 19.

For example, as illustrated in FIG. 4, the installation comprises at least two lateral fluidized bed zones (27, 29) connected one to each other wherein at least one fluidized bed zone 27 is the heating zone and at least one fluidized bed zone 29 is the reaction zone. For example, the heating zone 27 is surrounding the reaction zone 29. With preference, the installation comprises one or more fluid nozzles 23 arranged to inject a hydrocarbon feedstock and optionally steam to the at least one reaction zone 29 by means of a distributor 33. The fluidized bed zones (27, 29) further comprise optionally an inlet 7 for the material loading and a gas outlet 11. With preference, the at least one fluidized bed zone being the heating zone 27 and/or the at least one fluidized bed zone being the reaction zone 29 is devoid of heating means. For example, the at least one fluidized bed zone being the reaction zone 29 shows optionally an outlet 9 for the material discharge. One or more fluid nozzles 21 provide a fluidizing gas to at least the heating zone from a distributor 31. With one or more inlet devices 41, heated particles are transported from the heating zone 27 to the reaction zone 29, and with one or more means comprising downcomers, the separated particles are transported from the reaction zone 29 back to the heating zone 27. The fluidization gas for the heating zone 27 can be an inert diluent, like one or more selected from steam, hydrogen, methane, carbon dioxide, argon, helium and nitrogen. In such a configuration the fluidization gas for the heating zone can also comprise air or oxygen to burn deposited coke from the particles.

For example, as illustrated in FIG. 5, the installation comprises at least two fluidized bed reactors (37, 39) connected one to each other wherein at least one fluidized bed reactor 37 is the heating zone 27 and at least one fluidized bed reactor 39 is the reaction zone 29. With preference, the installation comprises one or more fluid nozzles 23 arranged to inject a hydrocarbon feedstock and optionally steam to the at least one fluidized bed reactor 39 being the reaction zone 29. The fluidized bed reactors (37, 39) further comprise optionally an inlet 7 for the material loading and a gas outlet 11. With preference, the at least one fluidized bed reactor 37 being the heating zone 27 and/or the at least one fluidized bed reactor 39 being the reaction zone 29 is devoid of heating means. For example, the at least one fluidized bed reactor 39 being the reaction zone 29 shows optionally an outlet 9 for the material discharge. By means of the inlet device 41 heated particles are transported from the heating zone 27 to the reaction zone 29 when necessary, and by means of device 35 the separated particles after the reaction zone are transported from the reaction zone back to the heating zone. The fluidization gas for the heating zone can be an inert diluent, like one or more selected from steam, hydrogen, methane, carbon dioxide, argon, helium, and nitrogen. In such a configuration the fluidization gas for the heating zone can also comprise air or oxygen to burn deposited coke from the particles.

For example, the at least one fluidized bed reactor 37 being the heating zone 27 comprises at least two electrodes 13 whereas the at least one fluidized bed reactor 39 being the reaction zone 29 is devoid of electrodes.

For example, the at least two fluidized bed reactors (37, 39) are connected one to each other by means 41 suitable to transport the particles from the heating zone 27 to the reaction zone 29, such as one or more lines.

For example, the at least two fluidized bed reactors (37, 39) are connected one to each other by means 35 suitable to transport the particles from the reaction zone 29 back to the heating zone 27, such as one or more lines.

The Catalytic Cracking Reaction

For example, the catalytic cracking reaction is conducted at a temperature ranging from 550° C. to 800° C., preferably from 600° C. to 750° C., more preferably from 650° C. to 700° C.

For example, the catalytic cracking reaction is performed at a pressure ranging between 0.1 MPa and 10.0 MPa, preferably between 0.5 MPa and 5.0 MPa.

In an embodiment, said process comprises a step of pre-heating with a gaseous stream said fluidized bed reactor before conducting said endothermic catalytic cracking reaction in the fluidized bed reactor; with preference, said gaseous stream is a stream of inert gas and/or has a temperature comprised between 500° C. and 800° C. The said embodiment is of interest when the electrically conductive particles of the bed have too high resistivity at room temperature to start the electro-heating of the bed.

For example, said endothermic catalytic cracking of hydrocarbons is performed at a weight hourly space velocity (defined as the ratio of mass flow of reaction stream to the mass of solid particulate material in the fluidized bed) of said reaction stream comprised between 0.1 $h^{-1}$ and 100 $h^{-1}$, preferably comprised between 1.0 $h^{-1}$ and 50 $h^{-1}$, more preferably comprised between 1.5 $h^{-1}$ and 10 $h^{-1}$, even more preferably comprised between 2.0 $h^{-1}$ and 6.0 $h^{-1}$. The weight hourly space velocity is defined as the ratio of mass flow of the reaction stream to the mass of solid particulate material in the fluidized bed.

The hydrocarbon feedstock for the present process is selected from C4 hydrocarbons (olefins and paraffins), straight run naphtha, catalytic cracking naphtha (comprising olefins and paraffins), steam cracker pyrolysis gasoline, coker naphtha, and olefin rich by-products from methanol, dimethyl ether, methyl halide, methyl sulphide or di-methyl sulphide conversion or from Fischer-Tropsch synthesis.

For example, the fluid stream provided in step b) comprises a hydrocarbon feedstock, in which the hydrocarbons have at least four carbons. The fluid stream may be a gaseous stream and/or a vaporized stream.

Petroleum naphtha or straight run naphtha is defined as the hydrocarbons fraction of petroleum having a boiling point from 15° C. up to 200° C. It is a complex mixture of linear and branched paraffins (single and multi-branched), cyclic paraffins and aromatics having carbons numbers ranging from 5 to about 11 carbons atoms. Light naphtha has a boiling range from to 90° C. and comprises C5 to C6 hydrocarbons, while heavy naphtha has a boiling range from 90 to 200° C. and comprises C7 to about C11 hydrocarbons. Naphtha is generally obtained in a crude oil refinery by distillation or obtained from condensates in natural gas processing.

The hydrocarbon feedstocks comprise C4 mixtures from refineries and steam cracking units. Such steam cracking units crack a wide variety of feedstocks, including ethane, propane, butane, naphtha, gas oil, fuel oil, etc. Most particularly, the hydrocarbon feedstock may comprise a C4 cut from a fluidized-bed catalytic cracking (FCC) unit in a crude oil refinery which is employed for converting heavy oil into gasoline and lighter products. Typically, such a C4 cut from an FCC unit comprises around 30-70 wt. % olefin. Alternatively, the hydrocarbon feedstock may comprise a C4 cut from a unit within a crude oil refinery for producing methyl tert-butyl ether (MTBE) or ethyl tert-butyl ether (ETBE) which is prepared from methanol or ethanol and isobutene. Again, such a C4 cut from the MTBE/ETBE unit typically comprises around 50 wt % olefin. The hydrocarbon feedstock may yet further comprise a $C_4$ cut from a naphtha steam-cracking unit of a petrochemical plant in which naphtha, comprising $C_5$ to $C_9$ species having a boiling point range of from about 15 to 200° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10% n-butane and/or isobutane. The olefin-containing hydrocarbon feedstock may also comprise a $C_4$ cut from a steam cracking unit after butadiene extraction (raffinate 1), or after butadiene hydrogenation.

The feedstock may yet further alternatively comprise a hydrogenated butadiene-rich $C_4$ cut, typically containing greater than 50 wt. % $C_4$ as an olefin. Alternatively, the hydrocarbon feedstock could comprise a pure olefin feedstock that has been produced in a petrochemical plant.

The olefin-containing feedstock may yet further alternatively comprise light cracked naphtha (LCN) (otherwise known as light catalytic cracked spirit (LCCS)) or a $C_5$ pyrolysis gasoline cut from a steam cracker or light cracked naphtha, the light cracked naphtha being fractionated from the effluent of the FCC unit, discussed hereinabove, in a crude oil refinery. Both such feedstocks contain olefins. The olefin-containing feedstock may yet further alternatively comprise a medium cracked naphtha from such an FCC unit or visbroken or coker naphtha obtained from a visbreaking or coker unit for treating the residue of a vacuum distillation unit in a crude oil refinery.

The feedstock may comprise a mixture of one or more of the above-described feedstocks.

As regards the feedstock and according to a specific embodiment of the invention the hydrocarbon feedstock containing one or more olefins is made in part or completely of the heavy hydrocarbon fraction coming from an XTO reactor. An XTO reactor is fed with oxygen-containing, halogenide-containing or sulphur-containing organic compounds and said are converted in said XTO reactor to olefin products (the effluent of the XTO). Said effluent comprises light olefins and a heavy hydrocarbon fraction. "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. The effluents of the XTO are fractionated to recover the heavy hydrocarbon fraction. More than 60% by weight and advantageously more than 75% of the hydrocarbons having 4 carbon atoms or more are C4 to C8 olefins.

In particular, the cracking products obtained in the present process may include one or more of ethylene, propylene and benzene, and optionally hydrogen, toluene, xylenes.

In a preferred embodiment, the outlet temperature of the reactor may range from 500 to 750° C., preferably from 550 to 700° C., more preferably from 600 to 650° C.

In a preferred embodiment, the catalytic cracking reaction performed on the hydrocarbon feedstock is done in presence of dilution steam in a ratio of 0.1 to 1.0 kg steam per kg of hydrocarbon feedstock, preferably from 0.15 to 0.7 kg steam per kg of hydrocarbon feedstock, more preferably in a ratio from 0.25 to 0.6 kg steam per kg of hydrocarbon feedstock, to obtain cracking products as defined above.

In a preferred embodiment, the catalytic cracking reaction is performed in the presence of hydrogen in a ratio of 0.1 to 5 moles hydrogen per mole of hydrocarbon feedstock, preferably from 0.2 to 3 and most preferably from 0.2 to 1.0.

In a preferred embodiment, the reactor outlet pressure may range from 0.050 to 0.250 MPa, preferably from 0.070 to 0.200 MPa, more preferably may be about 0.15 MPa. Lower operating pressure results in more light olefins yield and reduced coke formation. The lowest pressure possible is accomplished by (i) maintaining the output pressure of the reactor as close as possible to atmospheric pressure at the suction of the cracked gas compressor (ii) reducing the partial pressure of the hydrocarbons by dilution with steam (which has a substantial influence on slowing down coke formation).

The effluent from the catalytic cracking comprises unreacted feedstock, desired olefins (mainly ethylene and propylene), hydrogen, methane, a mixture of C4's, gasoline, aromatics in the C6 to C8 range.

The invention claimed is:

1. A process to perform an endothermic catalytic cracking of one or more hydrocarbons having at least four carbons, comprising:
   a) providing at least one fluidized bed reactor comprising at least two electrodes and a bed comprising particles, wherein:
      i) the particles of the bed comprise electrically conductive particles and particles of a catalytic composition;
      ii) the catalytic composition comprises from 5.0 to 90.0 wt. % of one or more zeolites based on the total weight of the catalyst composition, the zeolite comprises at least one 10-membered ring channel;
      iii) at least 10 wt. % of the particles based on the total weight of the particles of the bed are electrically conductive particles and have a resistivity ranging from 0.001 Ohm.cm to 500 Ohm.cm at 500° C.; and
      iv) a void fraction of the bed ranges from 0.5 to 0.8;
   b) injecting a fluid stream upwardly through the bed to putting the particles of the bed in a fluidized state thereby obtaining a fluidized bed;
   c) heating the fluidized bed to a temperature ranging from 500° C. to 850° C. by passing an electric current through the fluidized bed and cracking the hydrocarbons by endothermic catalytic cracking reaction; and
   d) optionally recovering the cracking products of the reaction.

2. The process according to claim 1, characterized in that the at least one fluidized bed reactor comprising the at least two electrodes and the bed comprising particles is devoid of packing.

3. The process according to claim 1, characterized in that from 50 wt. % to 100 wt. % of the electrically conductive particles of the bed based on the total weight of the electrically conductive particles of the bed are selected from the group consisting of one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

4. The process according to claim 1, characterized in that the electrically conductive particles of the bed are or comprise one or more non-metallic resistors selected from silicon carbide, molybdenum disilicide or a mixture thereof.

5. The process according to claim 1, characterized in that the electrically conductive particles of the bed are or comprise one or more mixed oxides being doped with one or more lower-valent cations which are one or more oxides having a cubic fluorite structure being at least partially substituted with one or more lower-valent cations and wherein said one or more lower-valent cations are selected from the group consisting of Sm, Gd, Y, Sc, Yb, Mg, Ca, La, Dy, Er, and Eu.

6. The process according to claim 5, characterized in that the mixed oxides being doped with one or more lower-valent cations are selected from the group consisting of:
   one or more $ABO_3$-perovskites with A and B tri-valent cations, being at least partially substituted in A position with one or more lower-valent cations and comprising at least one of Ni, Ga, Co, Cr, Mn, Sc, Fe and/or a mixture thereof in B position, and wherein said one or more lower-valent cations are selected from the group consisting of Ca, Sr, and Mg;
   one or more $ABO_3$-perovskites with A bi-valent cation and B tetra-valent cation, being at least partially substituted with one or more lower-valent cations in the B position occurs or with a mixture of different B elements in the B position and wherein the one or more lower-valent cations are selected from magnesium, scandium, yttrium, neodymium or ytterbium; and
   one or more $A_2B_2O_7$-pyrochlores with A tri-valent cation and B tetra-valent cation being at least partially substituted in A position with one or more lower-valent cation and comprising at least one of Sn, Zr and Ti in B position and wherein the one or more lower-valent cations are selected from Ca or Mg.

7. The process according to claim 1, characterized in that the electrically conductive particles of the bed are or comprise one or more metallic alloys.

8. The process according to claim 1, characterized in that the electrically conductive particles of the bed are or comprise one or more superionic conductors selected from the group consisting of $LiAlSiO_4$, $Li_{10}GeP_2S_{12}$, $Li_{3.6}Si_{0.6}P_{0.4}O_4$, sodium superionic conductors, and sodium beta alumina.

9. The process according to claim 1, characterized in that the one or more hydrocarbons having at least four carbons are selected from the group consisting of butenes, butanes, straight run naphtha, catalytic cracked naphtha, pyrolysis gasoline, coker and visbroken naphtha.

10. The process according to claim 1, characterized in that the cracking products comprise one or more of ethylene, propylene and benzene, and optionally hydrogen, toluene, xylenes.

11. The process according to claim 1, characterized in that said one or more zeolites are selected from the list comprising MFI, MEL, MTW, MTT and/or FER families and in that said one or more zeolites have a Si/Al molar ratio comprised between 20 and 5000.

12. The process according to claim 1, characterized in that said one or more zeolites further comprise one or more metal compounds which are one or more selected from the group consisting of group-2 elements, from group-4 elements, from group-11 elements, from one or more elements selected from the group consisting of Ce, Sn, Co, Mo, Mn, Ni, Fe, Cr, Pt, Pd, In, Ga, Re, W and V, and from rare earth elements.

13. The process according to claim 1, characterized in that the catalytic composition comprises a catalytic support selected from the group comprising alumina, alumina sol, titania, zirconia, quartz, silica, silica sol, silica-alumina, silica-magnesia, silica-zirconia, silica-thoria, silica-beryllia, silica-titania, calcium-alumina, calcium-silicate, ceria-zirconia-alumina, ceria-titania-alumina, ceria-magnesia-alumina, calcium-silica-alumina, silica-alumina-zirconia, hafnia, lanthania, magnesia, ceria, zirconia stabilized with magnesia, zirconia stabilized with lanthania, zirconia stabilized with yttria, zirconia stabilized with ceria, alumina stabilized with lanthania, metal-aluminates, and mixture thereof.

14. The process according to claim 1, characterized in that said process comprises a step of pre-heating with a gaseous stream of inert gas said fluidized bed reactor before conducting said endothermic catalytic cracking reaction in the fluidized bed reactor.

15. The process according to claim 1, characterized in that, wherein the at least one fluidized bed reactor provided in step a) comprises a heating zone and a reaction zone and wherein the fluid stream provided in step b) is provided to the heating zone and comprises diluent gases, the step c) of heating the fluidized bed to a temperature ranging from 500° C. to 850° C. to conduct the catalytic cracking reaction of one or more hydrocarbons having at least four carbons comprises the following sub steps:
heating the fluidized bed to a temperature ranging from 500° C. to 850° C. by passing an electric current through the heating zone of the at least one fluidized bed,
transporting the heated particles from the heating zone to the reaction zone,
in the reaction zone, putting the heated particles in a fluidized state by passing upwardly through the said bed of the reaction zone a fluid stream comprising a hydrocarbon feedstock, and optional diluent gases to obtain a fluidized bed and to conduct the catalytic cracking reaction on the one or more hydrocarbons having at least four carbons, and
recovering the particles from the reaction zone and recycling them to the heating zone.

16. An installation to perform an endothermic catalytic cracking of one or more hydrocarbons having at least four carbons according to claim 1, said installation comprising at least one fluidized bed reactor, comprising:
a) at least two electrodes;
b) a reactor vessel;
c) one or more fluid nozzles for the introduction of a fluidizing gas and/or of a reaction stream within at least one fluidized bed reactor; and
d) a bed comprising particles wherein
i) the particles of the bed comprise electrically conductive particles and particles of a catalytic composition;
ii) the catalytic composition comprises from 5.0 to 90.0 wt. % of one or more zeolites based on the total weight of the catalyst composition, the zeolite comprises at least one 10-membered ring channel; and
iii) at least 10 wt. % of the particles based on the total weight of the particles of the bed are electrically conductive particles and have a resistivity ranging from 0.001 Ohm.cm to 500 Ohm.cm at 500° C.;
iv) the void fraction of the bed ranges from 0.5 to 0.8.

17. The installation according to claim 16, characterized in that at least one fluidized bed reactor (18, 19, 37, 39) is devoid of heating means selected from ovens, gas burners, hot plates, or any combination thereof.

18. The installation according to claim 16, characterized in that the at least one fluidized bed reactor (18, 19, 37, 39) comprises a heating zone (27) and a reaction zone (29), one or more fluid nozzles (23) to provide one or more hydrocarbons having at least four carbons to the reaction zone (29), and means (35) to transport the particles from the reaction zone (29) back to the heating zone (27).

19. The installation according to claim 18, characterized in that
it comprises at least two fluidized bed reactors (37, 39) connected one to each other wherein at least one reactor (37) is the heating zone (27) and at least another reactor (39) is the reaction zone (29); or
the at least one fluidized bed reactor (19) is a single one fluidized bed reactor wherein the heating zone (27) is the bottom part of the fluidized bed reactor (19) while the reaction zone (29) is the top part of the fluidised bed reactor (19), or
at least one fluidized bed (18) comprises at least two lateral zones being an outer zone and an inner zone wherein the outer zone is surrounding the inner zone, with the outer zone being the heating zone (27) and the inner zone being the reaction zone (29).

20. The installation according to claim 16, characterized in that the at least one fluidized bed reactor comprising at least two electrodes and a bed comprising particles is devoid of packing.

* * * * *